(12) United States Patent
Kishioka et al.

(10) Patent No.: US 11,397,162 B2
(45) Date of Patent: *Jul. 26, 2022

(54) FLOW-TYPE ION SELECTIVE ELECTRODE, ELECTROLYTE CONCENTRATION MEASURING DEVICE USING THE SAME, AND BIOCHEMICAL AUTOMATIC ANALYZER

(71) Applicant: Hitachi High-Tech Corporation, Tokyo (JP)

(72) Inventors: Atsushi Kishioka, Tokyo (JP); Yu Ishige, Tokyo (JP); Tetsuyoshi Ono, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 60 days.

This patent is subject to a terminal disclaimer.

(21) Appl. No.: 17/034,528

(22) Filed: Sep. 28, 2020

(65) Prior Publication Data

US 2021/0010970 A1 Jan. 14, 2021

Related U.S. Application Data

(62) Division of application No. 15/111,857, filed as application No. PCT/JP2015/051719 on Jan. 22, 2015, now Pat. No. 10,823,695.

(30) Foreign Application Priority Data

Jan. 31, 2014 (JP) .............................. JP2014-016777

(51) Int. Cl.
*G01N 27/333* (2006.01)
*G01N 33/49* (2006.01)
(Continued)

(52) U.S. Cl.
CPC .......... *G01N 27/333* (2013.01); *F16J 15/021* (2013.01); *G01N 27/413* (2013.01);
(Continued)

(58) Field of Classification Search
CPC .................................................... G01N 27/333
See application file for complete search history.

(56) References Cited

U.S. PATENT DOCUMENTS 4,496,512 A    1/1985   Marsoner et al.
4,662,208 A    5/1987   Metzner et al.
(Continued)

FOREIGN PATENT DOCUMENTS

JP    58-21852 U    2/1983
JP    58-179350 A   10/1983
(Continued)

OTHER PUBLICATIONS

International Search Report (PCT/ISA/210) issued in PCT Application No. PCT/JP2015/051719 dated Apr. 21, 2015, with English translation (four (4) pages).

(Continued)

*Primary Examiner* — Sadie White
(74) *Attorney, Agent, or Firm* — Crowell & Moring LLP

(57) ABSTRACT

There is provided an electrolyte measuring device that can decrease a liquid amount used for measurement, in which stable sealing can be provided in connecting passages of ion selective electrodes to each other with no gap, while maintaining high measurement accuracy of an existing ion selective electrode, and a residing sample liquid can be greatly decreased. In a flow-type ion selective electrode, a sealing member is used, which can be brought into intimate contact with a passage connecting unit to near a passage hole. A gap regulating member is provided to keep a gap between the electrodes constant and to prevent the sealing member from (Continued)

being excessively pressed. An electrode case has a structure suitable for the sealing member for allowing the alignment and holding of the sealing member.

14 Claims, 19 Drawing Sheets

(51) Int. Cl.
 *F16J 15/02* (2006.01)
 *G01N 27/413* (2006.01)
 *G01N 27/27* (2006.01)
(52) U.S. Cl.
 CPC ......... *G01N 33/4915* (2013.01); *G01N 27/27* (2013.01); *G01N 33/492* (2013.01)

(56) References Cited

U.S. PATENT DOCUMENTS

| | | | |
|---|---|---|---|
| 4,935,117 A | 6/1990 | Uematsu et al. | |
| 6,186,513 B1 | 2/2001 | Udagawa | |
| 2003/0029722 A1* | 2/2003 | Erdosy | G01N 33/4915 |
| | | | 204/435 |
| 2009/0007642 A1 | 1/2009 | Busby | |
| 2010/0175994 A1* | 7/2010 | Lee | B01L 3/502753 |
| | | | 204/416 |

FOREIGN PATENT DOCUMENTS

| | | |
|---|---|---|
| JP | 61-29751 A | 2/1986 |
| JP | 62-86548 U | 6/1987 |
| JP | 1-70155 U | 5/1989 |
| JP | 2-7560 U | 1/1990 |
| JP | 3-40558 U | 4/1991 |
| JP | 3-117755 U | 12/1991 |
| JP | 7-140106 A | 6/1995 |
| JP | 10-318973 A | 12/1998 |
| JP | 11-111382 A | 4/1999 |
| JP | 11-132991 A | 5/1999 |
| JP | 2003-207476 A | 7/2003 |
| JP | 2009-282226 A | 12/2009 |

OTHER PUBLICATIONS

Partial Supplementary European Search Report issued in counterpart European Application No. 15743409.3 dated Aug. 9, 2017 (15 pages).
Umezawa et al., "Potentiometric Selectivity Coefficients of Ion-Selective Electrodes Part I. Inorganic Cations", Pure Applied Chemistry., 2000, pp. 1851-2082, vol. 72, No. 10, (232 pages).
Umezawa et al., "Potentiometric Selectivity Coefficients of Ion-Selective Electrodes Part II. Inorganic Anions", Pure Applied Chemistry., 2002, pp. 923-994, vol. 74, No. 6, (72 pages).
JP2009282226A—Ichijo, Nagato english equivalent of the abstract (Year: 2009).

* cited by examiner

FIG. 19A
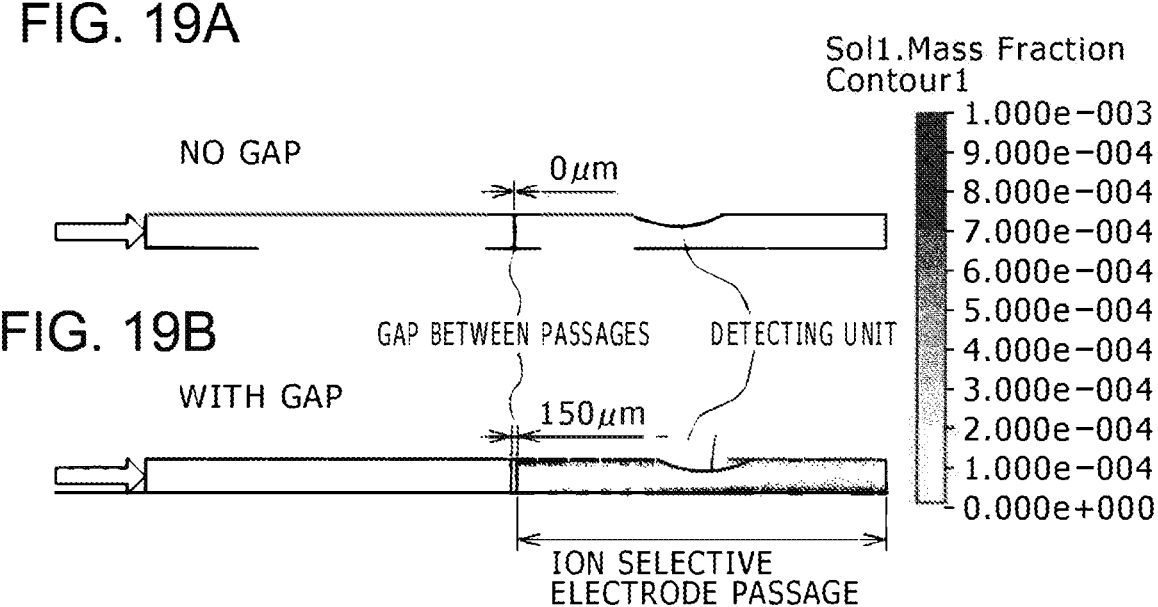
FIG. 19B
FIG. 20
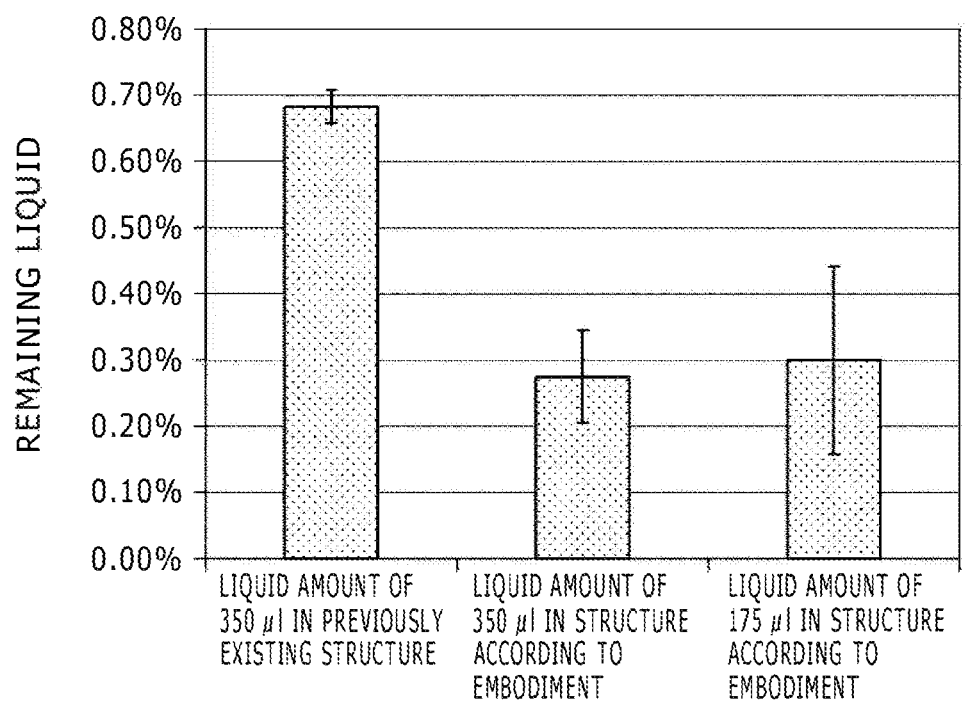

FIG. 21A
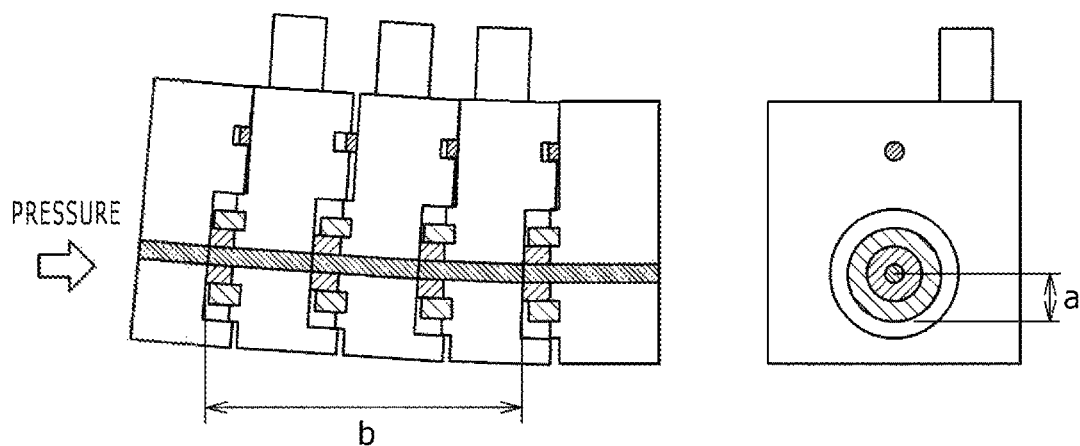
FIG. 21B
FIG. 22A
FIG. 22B
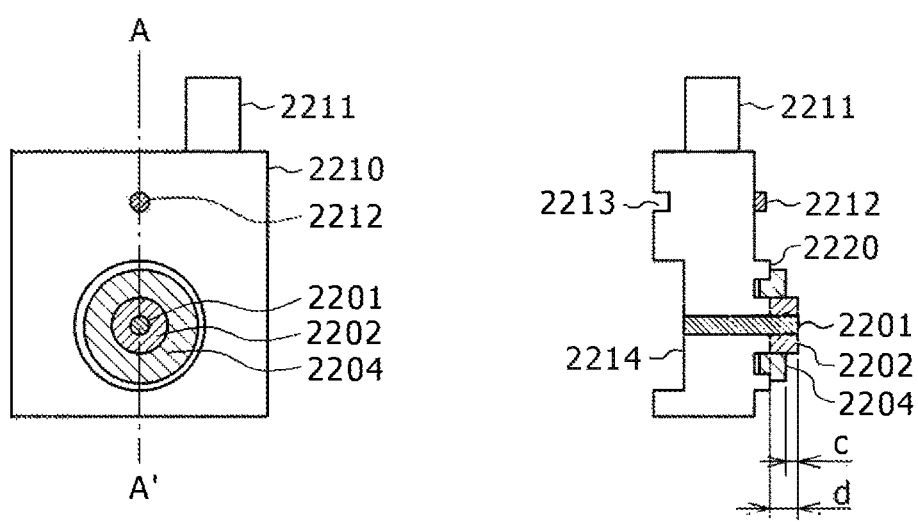

FLOW-TYPE ION SELECTIVE ELECTRODE, ELECTROLYTE CONCENTRATION MEASURING DEVICE USING THE SAME, AND BIOCHEMICAL AUTOMATIC ANALYZER

CROSS REFERENCE TO RELATED APPLICATIONS

This application is a divisional of U.S. patent application Ser. No. 15/111,857, filed Jul. 15, 2016, which is a 371 of International Application No PCT/JP2015/051719, filed Jan. 22, 2015, which claims priority to Japanese Patent Application No. 2014-016777, filed Jan. 31, 2014, the disclosures of all of which are expressly incorporated by reference herein.

TECHNICAL FIELD

The present invention relates to a flow-type ion selective electrode that measures the concentration of an electrolyte in a solution, an electrolyte concentration measuring device equipped with the electrode, and a biochemical automatic analyzer.

BACKGROUND ART

In an ion selective electrode (ISE), a sample liquid is brought into contact with a detecting unit, a potential difference between the ion selective electrode and a reference electrode is measured, and then a measurement target ion in a sample can be quantitatively measured. Because of such convenience, the ion selective electrode is widely used in analysis fields. Specifically, in a flow-type ion selective electrode, a detecting unit is provided on a passage through which a sample liquid is carried. Thus, ion concentrations of a plurality of samples can be sequentially quantitatively measured. Therefore, the flow-type ion selective electrode is used for clinical examinations in medical fields. The flow-type ion selective electrode is installed on special purpose devices for electrolyte measurement as well as installed on a biochemical automatic analyzer or an emergency specimen inspection apparatus as an electrolyte measuring unit (device).

In order to simultaneously detect a plurality of ions (e.g. a sodium ion, potassium ion, calcium ion, chlorine ion, and other ions), an electrolyte measuring unit is commonly installed with a plurality of ion selective electrodes corresponding to ions to be detected. Commonly, these electrodes are consumable items. For example, the electrodes consume their lifetime in two or three months, and replaced by new electrodes. The flow-type ion selective electrodes installed on the electrolyte measuring device have two types, i.e. an integrated type in which a plurality of ion selective electrodes is integrated, and a separate type in which ion selective electrodes are separately present. The separate type has a significant advantage in which only one electrode desired by a user can be replaced. For example, in the case where it is necessary to replace one of a plurality of electrodes installed on the electrolyte analyzer by a new electrode because of its use lifetime or its malfunction, the integrated type has to replace the malfunctioned electrode as well as normally operating electrodes, whereas the separate type can replace only one electrode that has to be replaced.

For an example of mounting separate type ion selective electrodes on an electrolyte analyzer, a method is disclosed in Patent Literature 1, in which a plurality of ion selective electrodes is stacked, an O-ring is disposed between the electrodes for connecting their passages to each other, and the plurality of electrodes is pressed from both sides for fixing the electrodes and for preventing a liquid from leaking. The separate type ion selective electrode has a problem specific to the electrode in that electrodes are detached from each other in mounting the electrodes on a device. In order to solve this problem, Patent Literature 1 discloses a shape in which a projection is faced to a groove and the projection is press-fit into the groove in order to allow electrodes to be held in intimate contact with each other. Patent Literature 2 discloses a shape in which a boss is formed in order to prevent an O-ring from easily being detached.

CITATION LIST

Patent Literature

Patent Literature 1: Japanese Unexamined Utility Model Application Publication No. Sho 62-86548
Patent Literature 2: Japanese Unexamined Utility Model Application Publication No. Hei 01-70155

SUMMARY OF INVENTION

Technical Problem

In the electrolyte analyzer, for example, reagents are used, including an internal standard solution to be a reference for measurement and a diluent for diluting a specimen, other than specimens. These reagents are consumable items, and need costs when purchased or discarded. In the case where it is necessary to replace a reagent bottle in continuous operation, the operation rate of the device is reduced. This raises a great demand for a decrease in the amount of a sample liquid in the electrolyte analyzer. Note that, in the following description, internal standard solutions and solutions containing a specimen or a diluent are referred to as samples or sample liquids. Because of the demand, the inventors conducted research and development in order to devise a device and a method that decrease the amount of a sample liquid in an electrolyte measuring device while maintaining high measurement accuracy of an existing ion selective electrode. As a result, it was revealed that a previously existing structure provided insufficient measurement accuracy when a liquid amount was decreased.

The configurations of the passage connecting unit of the electrode are disclosed in Patent Literatures 1 and 2, in which the O-ring is provided and the electrodes are brought into intimate contact with each other. These configurations sufficiently serve to prevent a liquid from leaking. However, the location of the passage hole is apart from the location at which the electrodes are brought into intimate contact with each other with the O-ring, which causes a sample liquid to reside in a gap between passages. It was found that in the case where a liquid amount that allowed the replacement of sufficient liquids was maintained, a measured result was hardly affected even though a gap was present between passages. However, a smaller amount of a sample liquid more greatly affects a remaining liquid in the gap between the passages. For example, let us consider the case where a sample liquid of high ion concentration, which is a measurement target, is measured and then a sample liquid of low concentration is measured. A gap is present between passages, and then a liquid of high concentration resides in the gap. When a low sample liquid of low concentration continuously flows on the gap, the high concentration liquid residing in the gap is gradually replaced.

FIG. 19 is a diagram of results of simulation for remaining liquids conducted by the inventors. An ion selective electrode is provided, in which a passage has a diameter of 1 mm and a length of 10 mm and a detecting unit appearing with a curved surface is provided in the midway point of the passage. A passage in the same size is connected to the upstream side of the passage of the electrode. This is modeled into a case (a) where no gap is present between the passages and a case (b) where a gap in a length of 150 μm is present between the passages. Note that, the end of the gap in a length of 150 μm is sealed with an O-ring, and a distance from the passage to the inner diameter of the O-ring was set to 1 mm. For simulation software, ANSYS 13.0 made by ANSYS, Inc. using Finite Element Method CAE was used. Simulation was conducted as follows. First, the passages were filled with a liquid of concentration 1, and then a liquid of concentration 0 is carried for one second at a flow rate of 175 μL. As a result, in the case (a) with no gap, the liquid in the passages was replaced by the liquid of concentration 0. In the case (b) with the gap, a liquid of high concentration remained in the gap, and the liquid of high concentration ran on the surface. Specifically, concentration near the surface of the detecting unit, which existed on the surface, was high. It was confirmed that the residing liquid, which was present near the surface at high concentration, was highly likely to greatly affect the ion selective electrode, which was a surface sensor. In order to control the gap between the passages in the previously existing structure, it is necessary to accurately control shaping an electrode case and the O-ring and a pressure to bring the electrodes into intimate contact with each other. In the case of the separate type, many passage connecting units are present, compared with the integrated type electrode, easily causing the gap between the passages. Note that, in the following description, the flow-type ion selective electrode is referred to as anion selective electrode, unless otherwise specified.

As described above, in order to decrease the liquid amount with high measurement accuracy being maintained, it is necessary to decrease the gap between the passages at the passage connecting unit.

Therefore, an object of the present invention is to provide an electrolyte measuring device that can decrease a liquid amount used for measurement, in which stable sealing can be provided in connecting passages of ion selective electrodes to each other with no gap, while maintaining high measurement accuracy of an existing ion selective electrode, and a residing sample liquid can be greatly decreased.

Solution to Problem

In order to solve the problem, an example of an ion selective electrode according to an aspect of the present invention has a feature below, which is an ion selective electrode including: a passage penetrated through a case; a detecting unit that detects an ion in a sample liquid carried through the passage; and a passage connecting unit that connects a passage provided on another case to supply the sample liquid or connects a passage provided on another case to discharge the sample liquid. In the ion selective electrode, the passage connecting unit includes a sealing member that seals a gap between the passage of the case and the case to supply the sample liquid or the case to discharge the sample liquid in the connection. The sealing member includes a sheet and a projection. Rubber hardness of a material configuring the sealing member is lower than rubber hardness of a material configuring of the case. The passage connecting unit is provided with a recess for holding the sealing member. The sealing member is provided with an opening in a diameter equal to a passage diameter or greater at a position of an end portion of the passage.

An example of an electrolyte concentration measuring device according to an aspect of the present invention has a feature below, which is an electrolyte concentration measuring device including: an upstream side connecting unit disposed on an upstream side from which a sample liquid is supplied; a downstream side connecting unit disposed on a downstream side from which the sample liquid is discharged; and a flow-type ion selective electrode joined between the upstream side connecting unit and the downstream side connecting unit. In the electrolyte concentration measuring device, the ion selective electrode includes a case, a passage penetrated through the case, a detecting unit that detects an ion in a sample liquid carried through the passage, a first passage connecting unit provided on one side surface of the case, and a second passage connecting unit provided on another side surface opposed to the one side surface. The first passage connecting unit includes a sealing member that seals a gap between the passage of the case and another case in connection. The second passage connecting unit includes a detachable connecting unit that allows connection to a first passage connecting unit provided on the case to supply the sample liquid or the case to discharge the sample liquid. The sealing member includes a sheet and a projection. Rubber hardness of a material configuring the sealing member is lower than rubber hardness of a material configuring of the case. The first passage connecting unit includes a recess for holding the sealing member. In connecting the case to supply the sample liquid or the case to discharge the sample liquid to the case with the first passage connecting unit, a cross sectional area of the sealing member is increased by pressing force applied to the sealing member. The sealing member is adjusted so that a side surface of the sealing member with the increased cross sectional area reaches a position in contact with an extension line of an outer circumferential portion of the passage, or reaches a position of the passage on an inner side of the extension line.

Advantageous Effects of Invention

According to an aspect of the present invention, there can be provided an electrolyte measuring device that can decrease a liquid amount used for measurement, in which stable sealing can be provided in connecting passages of ion selective electrodes to each other with no gap while maintaining high measurement accuracy of an existing ion selective electrode, and a residing sample liquid can be greatly decreased.

BRIEF DESCRIPTION OF DRAWINGS

FIGS. 19A and 19B are a diagram of results of simulation for remaining liquids.

FIG. 20 is a diagram of a result of remaining liquid confirmation experiments.

FIGS. 21A and 21B are schematic diagrams of an example of joining state of a measuring unit to ion selective electrodes.

FIGS. 22A and 22B are schematic diagrams of an example of structure of a passage connecting unit of an ion selective electrode according to the present invention.

DESCRIPTION OF EMBODIMENTS

Figure 1A:
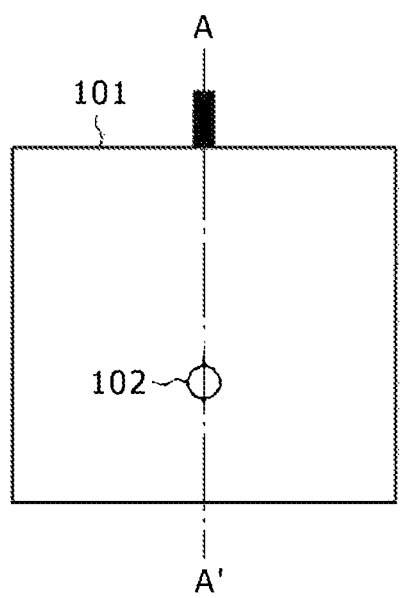
FIGS. 1A-1C are schematic diagrams of an example of ion selective electrode.

Problems, configurations, and effects other than ones describe above will be apparent from the description of an embodiment below.

In the following, referring to the drawings, an embodiment of the present invention will be described.

Figure 1B:
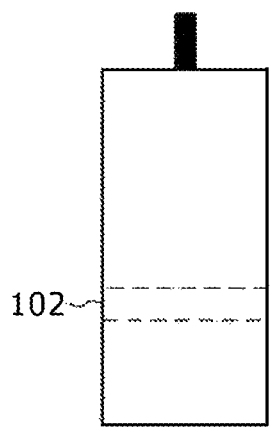
Figure 1C:
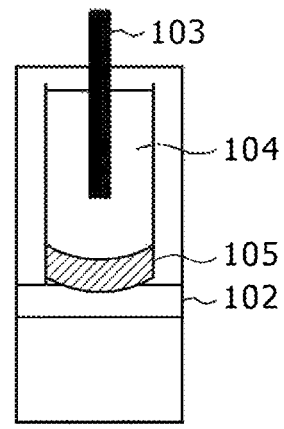

FIG. 1 are schematic diagrams of an example of ion selective electrode. Note that, in these drawings, a passage connecting unit is schematically illustrated, the detail of which will be described later. Through a rigid plastic case 101 of an ion selective electrode, a passage 102 is penetrated. (a) is a diagram of a face perpendicular to a passage. (b) is a diagram of a face parallel with the passage. (c) is a diagram of a cross section taken along chain line A-A' in (a).

As illustrated in (c), a sensitive membrane 105, which is a detecting unit, is in contact with the passage 102. On the opposite side of the passage 102, the case 101 is filled with an internal liquid 104. A silver-silver chloride electrode 103 is in contact with the internal liquid 104. The silver-silver chloride electrode 103 also serves as a terminal. For a positive ion selective electrode for sodium, potassium, calcium, magnesium, and the like, there can be used for the sensitive membrane 105, for example, a membrane containing an ionophore, such as crown ether, described in Pure Appl. Chem., Vol. 72, No. 10, pp. 1851-2082, 2000. For a negative selective electrode for chlorine, carbonic acid, thiocyanogen, nitric acid, hydroxide, phosphoric acid, sulfuric acid, iodine, and the like, in addition to a membrane containing an ionophore described in Pure Appl. Chem., Vol. 74, No. 6, pp. 923-994, 2002, there can be used silver halide, such as silver chloride and silver bromide, and an ion exchange membrane (Japanese Unexamined Patent Application Publication Nos. Hei 10 (1998)-318973, Hei 11 (1999)-132991, and 2003-207476). For a reference electrode, porous glass, ceramics, and the like can be used. However, any membranes can be used.

Here, the passage connecting unit of the ion selective electrode will be described. First, for comparison, an electrode structure disclosed in Patent Literature 1 will be described. FIG. 7 are schematic diagrams of an example of a previously existing structure of a passage connecting unit of an ion selective electrode. (a) is a diagram of a face perpendicular to a passage. (c) is a diagram of a face on the opposite side of the passage. (b) is a diagram of a cross section taken along chain line A-A' in (a). (d) is a diagram of a passage connecting unit when ion selective electrodes in the same shape are arranged side by side and pressed against each other.

The ion selective electrode is configured of a passage 701 penetrated through an electrode case 710, an O-ring 702, an electrode relative positioning projection 712, an electrode relative positioning groove 713, a terminal 711, a passage connecting projection 703, and a passage connecting recess 714. For example, in arranging electrodes in the same shape side by side and installing these electrodes on the device, the O-ring 702 is pressed against the passage connecting recess of the other electrode for functioning as a seal that prevents a sample liquid carried through the passage 701 from leaking.

However, in this structure, the passage 701 is apart from the O-ring 702, causing a gap 720 (see (d)). A sample liquid carried through the passage 701 resides in the gap 720. When the subsequent sample liquid is carried, the previous sample liquid is gradually carried through the passage 701 for a while.

As described above, this affects the measured result of the ion selective electrode, which is a surface sensor. However, in the case where a liquid amount used for measurement is large, carrying a sample liquid in an amount that allows sufficient replacement hardly affects measurement. However, in the case where a liquid amount is decreased, the remaining liquid that resides in the gap greatly affects measurement.

Figure 8A:
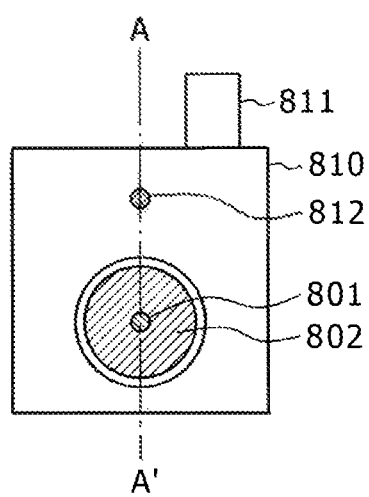
FIGS. 8A and 8B are schematic diagrams of an example of structure of a passage connecting unit of an ion selective electrode according to the present invention.
Figure 8B:
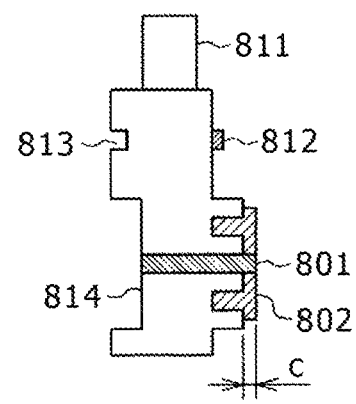

Next, the structure of the passage connecting unit according to the embodiment of the present invention will be described. FIG. 8 are schematic diagrams of an example of structure of the passage connecting unit of the ion selective electrode according to the embodiment of the present invention. (a) is a diagram of a face perpendicular to a passage. (b) is a diagram of a cross section taken along chain line A-A' in (a). The ion selective electrode is configured of a passage 801 penetrated through an electrode case 810, a sealing member 802, an electrode relative positioning projection 812, an electrode relative positioning groove 813, a terminal 811, and a passage connecting recess 814. Note that, in the description of the embodiment, the recess 814 is provided for connecting another electrode case different from an electrode case 810. Any connecting units that only have to be detachable can be used, such as a unit that applies pressing force to the sealing member 802 disposed between the electrode case and the other electrode case for press fitting the electrode case into the other electrode case, for example. A groove in the following description can be similarly used.

The sealing member is made of a material softer than the material of the case. The sealing member 802 has a flat sheet for sealing and a projection for holding and aligning the electrode case 810. The electrode case 810 has a recess for holding and aligning the sealing member 802. The sheet is provided with a hole at the position of the passage of the passage connecting unit in the same diameter as the diameter of the cross section of the passage, or greater. For example, in arranging the electrodes in the same shape side by side and installing the electrodes on the device, this structure allows the sealing member to be pressed against the passage connecting recess of the other electrode (e.g. FIG. 17) and to be sealed to near the passage. This eliminates the gap 720, which is produced in the structure in FIG. 7, and thus, the residing sample liquid is greatly decreased.

Commonly, a softer sealing member has better adhesion when pressed against the recess. However, in order to keep the shape and to maintain the sealing properties even though the pressing pressure is varied, the rubber hardness of the sealing part was set to 40 or more (durometer type A). The projection of the sealing member is formed in its width wider than the width of the alignment recess of the electrode case and in its length shorter than the length of the alignment recess. Thus, the sealing member 802 can be efficiently integrated with the electrode case 810 only by fitting the sealing member 802 into the electrode case 810, with no necessity of an adhesive or welding.

In replacing and handling the electrode, the detachment of the sealing member causes complicated manipulation. Thus, reliably holding the sealing member on the electrode case is a significant advantage to a separate type electrode. The electrode case uses injection molding plastic, and its flat surface accuracy is not so excellent. Thus, in the case where the sealing member is too thin, the absorption of surface roughness of the body fails, causing a reduction in the sealing properties. Consequently, a thickness c of the sheet was set to 0.01 mm or more, which is the thickness that enables reliable sealing properties.

Figure 9A:
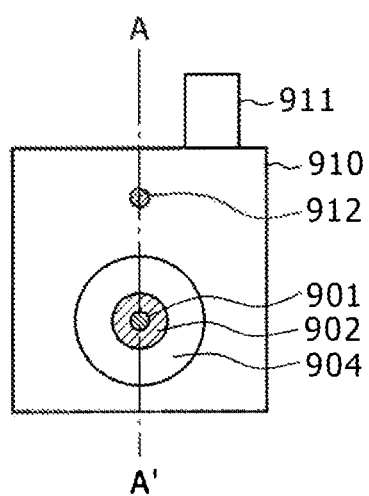
FIGS. 9A and 9B are schematic diagrams of another exemplary structure of a passage connecting unit of an ion selective electrode according to the present invention.
Figure 9B:
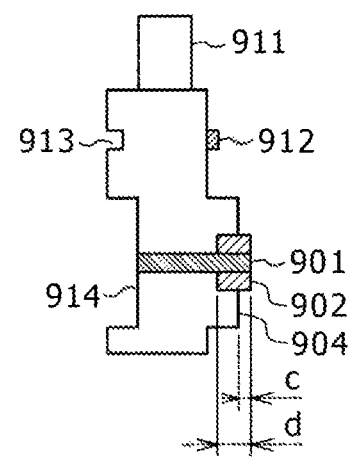

FIG. 9 are schematic diagrams of another exemplary structure of the passage connecting unit of the ion selective electrode according to the embodiment of the present invention. (a) is a diagram of a face perpendicular to a passage. (b) is a diagram of a cross section taken along chain line A-A' in (a). The ion selective electrode is configured of a passage 901 penetrated through an electrode case 910, a sealing member 902, an electrode relative positioning projection 912, an electrode relative positioning groove 913, a terminal 911, and a passage connecting recess 914. The sealing member is made of a material softer than the material of the case. The sealing member is provided with a hole at the position of the passage of the passage connecting unit in the same diameter as the diameter of the cross section of the passage, or greater. The electrode case 910 has a recess for holding and aligning the sealing member 902. The sealing member 902 is integrated only by fitting the sealing member 902 into the recess of the electrode case for holding the sealing member. The portion of the electrode case, at which the sealing member is provided, functions as a gap regulating portion 904. For example, in arranging the electrodes in the same shape side by side and installing the electrodes on the device, pressing the sealing member at a pressure in a specified range (e.g. 5 to 50 N) causes the gap regulating portion 904 to be contacted with the recess 914 of another electrode. Thus, the gap regulating portion 904 serves to keep a constant gap between the electrodes and to prevent the sealing member from being excessively pressed. With this structure, in installing a combination of the electrodes on the device, the sealing member is moderately pressed against the passage connecting recess of the other electrode, and the sealing member is sealed to near the passage. Thus, the residing sample liquid is greatly decreased. Even though the electrodes are installed on a device having a different pressing pressure, the sealing member is uniformly pressed, allowing stable connection of the passages.

The outer diameter of the sealing member is formed larger than the inner diameter of the recess of the electrode case for holding the sealing member. This allows the efficient integration of the electrodes only by fitting the sealing member 902 into the electrode case 910. In replacing and handling the electrode, the detachment of the sealing member causes complicated manipulation. Thus, reliably holding the sealing member on the electrode case is a significant advantage to a separate type electrode. In the case where the sealing member is too thin, the absorption of surface roughness of the body fails, causing a reduction in the sealing properties. Consequently, a protruding height c of the sealing member was set to 0.01 mm or more. In the case where the collapsing amount of the sealing member is large, the sealing member protrudes and narrows the passage and disturbs the liquid current. Thus, the sealing member was designed in such a manner that a value in which the protruding height c of the sealing member is divided by a total length d of the sealing member is 0.4 or less.

Figure 10A:
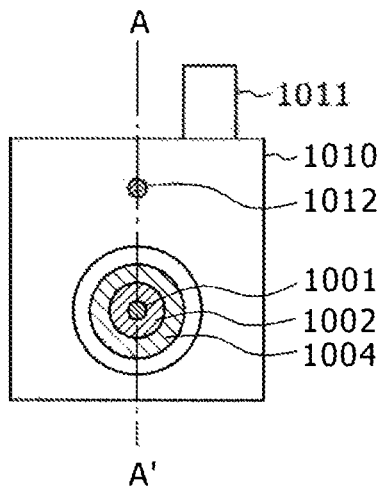
FIGS. 10A and 10B are schematic diagrams of another exemplary structure of a passage connecting unit of an ion selective electrode according to the present invention.
Figure 10B:
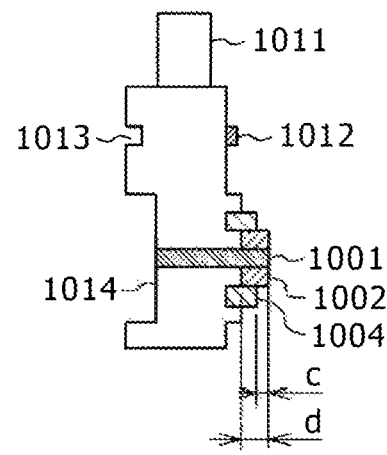

FIG. 10 are schematic diagrams of another exemplary structure of the passage connecting unit of the ion selective electrode according to the embodiment of the present invention.

(a) is a diagram of a face perpendicular to a passage. (b) is a diagram of a cross section taken along chain line A-A' in (a). The ion selective electrode is configured of a passage 1001 penetrated through an electrode case 1010, a sealing member 1002, a gap regulating member 1004, an electrode relative positioning projection 1012, an electrode relative positioning groove 1013, a terminal 1011, and a passage connecting recess 1014. The sealing member is made of a material softer than the material of the case. The gap regulating member is made of a material harder than the material of the sealing member. The sealing member is provided with a hole at the position of the passage of the passage connecting unit in the same diameter as the diameter of the cross section of the passage, or greater.

The electrode case 1010 has a recess for holding and aligning the gap regulating member 1004. The gap regulating member 1004 is integrated only by fitting the gap regulating member 1004 into the recess of the electrode case for holding the gap regulating member. The outer diameter of the sealing member 1002 is formed greater than the inner diameter of the gap regulating member 1004. The sealing member 1002 is integrated by fitting the sealing member 1002 into the gap regulating member 1004. Alternatively, in order to more firmly hold the sealing member, the contacting parts of the sealing member to the gap regulating member may be attached in advance by welding or using an adhesive. In replacing and handling the electrode, the detachment of the sealing member causes complicated manipulation. Thus, reliably holding the sealing member on the electrode case is a significant advantage to a separate type electrode.

For example, in arranging the electrodes in the same shape side by side and installing the electrodes on the device, pressing the sealing member at a pressure in a specified range (e.g. 5 to 50 N) causes the gap regulating portion 1004 to be contacted with the recess 1014 of another electrode. Thus, the gap regulating portion 1004 serves to keep a constant gap between the electrodes and to prevent the sealing member from being excessively pressed. With this structure, in installing a combination of the electrodes on the device, the sealing member is moderately pressed against the passage connecting recess of the other electrode, and the sealing member is sealed to near the passage. Thus, the residing sample liquid is greatly decreased. Even though the electrodes are installed on a device having a different pressing pressure, the sealing member is uniformly pressed, allowing stable connection of the passages. In the case where the sealing member is too thin, the absorption of surface roughness of the body fails, causing a reduction in the sealing properties. Consequently, the protruding height c of the sealing member was set to 0.01 mm or more. In the case where the collapsing amount of the sealing member is large, the sealing member protrudes and narrows the passage and disturbs the liquid current. Thus, the sealing member was designed in such a manner that a value in which the protruding height c of the sealing member is divided by the total length d of the sealing member is 0.4 or less.

FIG. 22 are schematic diagrams of an example of structure of the passage connecting unit of the ion selective electrode according to the embodiment of the present invention. The basic configuration is the same as that in FIG. 10. However, the shape of the gap regulating member is different from that in FIG. 10. In FIG. 10, the gap is regulated based on the bottom face of the recess for holding the gap regulating member. In FIG. 22, a gap regulating member 2204 is not in contact with the bottom face of the recess for holding the gap regulating member. The gap regulating member 2204 is in contact with a flat face 2220 of the electrode case, and the gap is regulated base on the flat face 2220.

Figure 11A:
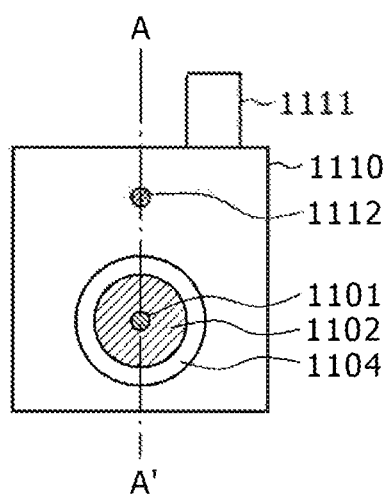
FIGS. 11A and 11B are schematic diagrams of another exemplary structure of a passage connecting unit of an ion selective electrode according to the present invention.
Figure 11B:
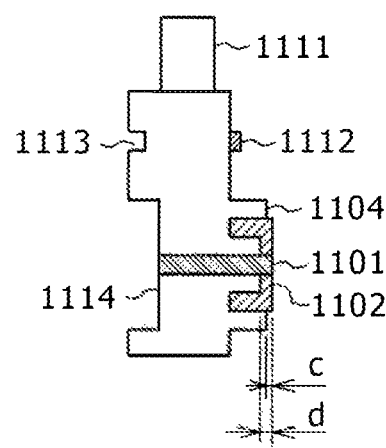
Figure 12A:
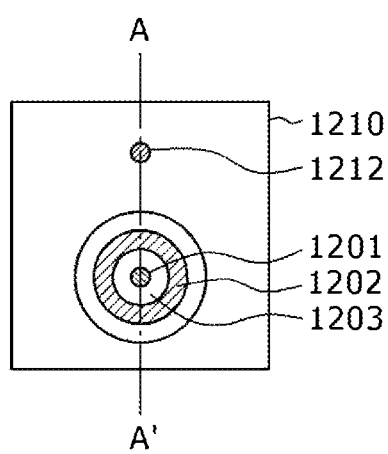
FIGS. 12A-12D are schematic diagrams of an example of a previously existing structure of a passage connecting unit of a measuring unit.
Figure 12B:
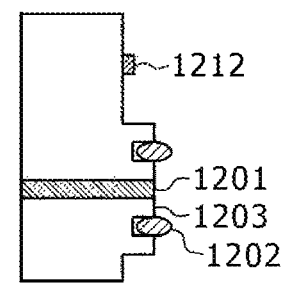
Figure 12C:
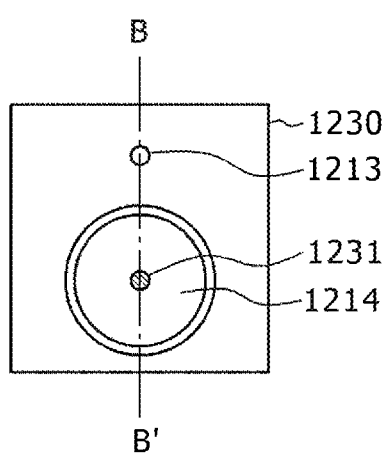
Figure 12D:
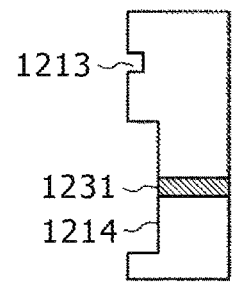

FIG. 11 are schematic diagrams of another exemplary structure of the passage connecting unit of the ion selective electrode according to the embodiment of the present invention. (a) is a diagram of a face perpendicular to a passage. (b) is a diagram of a cross section taken along chain line A-A' in (a). The ion selective electrode is configured of a passage 1101 penetrated through an electrode case 1110, a sealing member 1102, an electrode relative positioning projection 1112, an electrode relative positioning groove 1113, a terminal 1111, and a passage connecting recess 1114. The sealing member is made of a material softer than the material of the case. The sealing member 1102 has a flat sheet for sealing and a projection for holding and aligning the electrode case 1110. The electrode case has a recess for holding and aligning the sealing member.

The sheet is provided with a hole at the position of the passage of the passage connecting unit in the same diameter as the diameter of the cross section of the passage, or greater. The sealing member 1102 is integrated by fitting the sealing member 1102 into the recess of the electrode case 1110 for holding the sealing member. The portion of the electrode case, at which the sealing member is provided, functions as a gap regulating portion 1104. For example, in arranging the electrodes in the same shape side by side and installing the electrodes on the device, pressing the sealing member at a pressure in a specified range (e.g. 5 to 50 N) causes the gap regulating portion 1104 to be contacted with the recess 1114 of another electrode. Thus, the gap regulating portion 1104 serves to keep a constant gap between the electrodes and to prevent the sealing member from being excessively pressed.

With this structure, in installing a combination of the electrodes on the device, the sealing member is moderately pressed against the passage connecting recess of the other electrode, and the sealing member is sealed to near the passage. Thus, the residing sample liquid is greatly decreased. Even though the electrodes are installed on a device having a different pressing pressure, the sealing member is uniformly pressed, allowing stable connection of the passages. The projection of the sealing member is formed in its width wider than the width of the alignment recess of the electrode case and in its length shorter than the length of the alignment recess. Thus, this allows the efficient integration of the electrodes only by fitting the sealing member 1102 into the electrode case 1110. In replacing and handling the electrode, the detachment of the sealing member causes complicated manipulation. Thus, reliably holding the sealing member on the electrode case is a significant advantage to a separate type electrode. In the case where the sealing member is too thin, the absorption of surface roughness of the body fails, causing a reduction in the sealing properties. Consequently, the protruding height c of the sealing member was set to 0.01 mm or more. In the case where the collapsing amount of the sealing member is large, the sealing member protrudes and narrows the passage and disturbs the liquid current. Thus, the sealing member is designed in such a manner that a value in which the protruding height c of the sealing member is divided by the total length d of the sealing member (except the projection) is 0.4 or less.

Figure 24A:
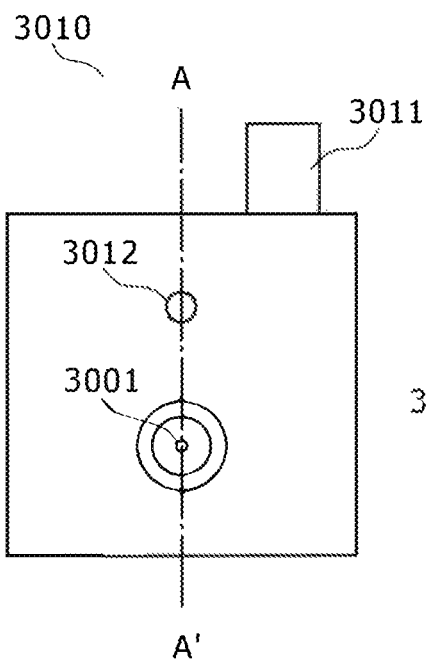
FIGS. 24A-24C are schematic diagrams of another exemplary structure of a passage connecting unit of an ion selective electrode according to the present invention.
Figure 24B:
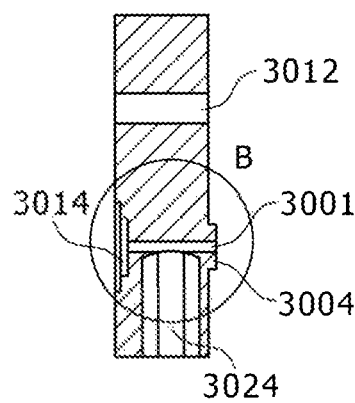
Figure 24C:
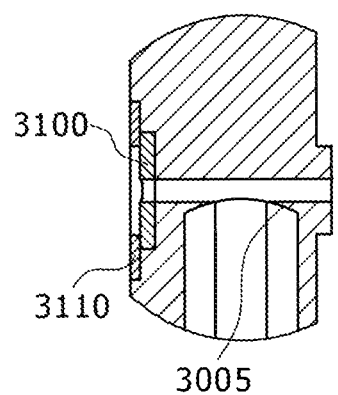

FIG. 24 are schematic diagrams of another exemplary structure of the passage connecting unit of the ion selective electrode according to the embodiment of the present invention. (a) is a diagram of a face perpendicular to a passage. (b) is a diagram of a cross section taken along chain line A-A' in (a). (c) is a diagram illustrating a region surrounded by circle B in (b) in detail. The ion selective electrode is configured of a passage 3001 penetrated through an electrode case 3010, a sealing member 3100, a holding member 3110, a positioning hole 3012, a terminal 3011, a passage connecting projection 3004, a passage connecting recess 3014, a sensitive membrane attaching portion 3005 at which a sensitive membrane (not illustrated) is disposed, a space 3024 for holding an internal liquid (not illustrated), and other components.

Figure 25:
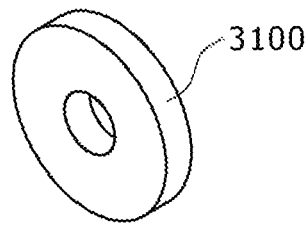
FIG. 25 is a schematic diagram of an example of structure of a sealing member of an ion selective electrode.

FIG. 25 is a bird's eye view of the outline of the structure of the sealing member 3100. The sealing member 3100 according to the embodiment is in nearly a tubular shape, and has a through hole in the center.

Figure 26:
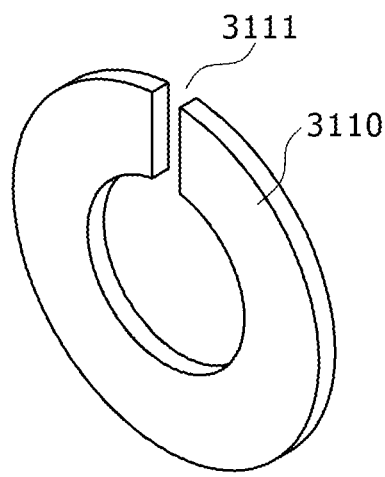
FIG. 26 is a schematic diagram of an example of structure of a holding member of an ion selective electrode.

FIG. 26 is a bird's eye view of the outline of the structure of the holding member 3110. The holding member 3110 according to the embodiment is in nearly a tubular shape, and has a through hole in the center and a slit 3111 on a part of the holding member 3110.

The sealing member is made of a material softer than the material of the case. The sealing member 3100 according to the embodiment basically has only a flat structure for sealing. Thus, the sealing member 3100 according to the embodiment is only formed of a portion corresponding to the sheet of the other examples of the present application. The sealing member 3100 can also be interpreted as the sealing member 3100 having no projection. The electrode case has the recess 3014 that serves to hold the sealing member, alignment, and connecting the passages.

The sheet is provided with a hole at the position of the passage of the passage connecting unit in the same diameter as the diameter of the cross section of the passage, or greater. The sealing member 3100 can be fit into the recess 3014 of the electrode case 3010. The sealing member 3100 is pressed by the holding member 3110, and thus integrated with the electrode case 3010. Specifically, as illustrated in FIG. 24, the recess 3014 has dents in two steps having different inner diameters. The sealing member 3100 is fit into the dent on the inner side (the back side). The holding member 3110 is fit into the dent on the outer side (the surface side). Thus, the sealing member 3100 is integrated with the electrode case 3010.

In the embodiment, the thickness of the sealing member 3100 was set to 0.5 mm. The height from the surface of the electrode case 3010 to the projecting portion of the projection 3004 was set to 0.5 mm. The depth from the surface of the electrode case 3010 to the face of the dent on the inner side of (the back side) of the recess 3014 was set to 0.9 mm. The outer diameter of the projection 3004 was set to 3 mm. The inner diameter of the through hole of the holding member 3110 is set to 3.1 mm. In the combination of the projection 3004 of the first electrode case with the recess 3014 (installed with the sealing member) of the second electrode case, the outer diameter of the projection 3004 of the first electrode case is smaller than the inner diameter of the through hole of the holding member 3110 provided on the recess 3014 of the second electrode case. Thus, the projection 3004 passes through the through hole of the holding member 3110. The thickness of the portion of combining the projection 3004 and the recess 3014 (installed with the sealing member) is thicker than the thickness of the other portions of the electrode case 3010 by 0.1 mm. When the first electrode case is pressed and contacted with the second electrode case, the difference in the thickness becomes the margin of the sealing member to collapse. The projection of the first electrode case is pressed and contacted with the surface of the sealing member 3100 provided on the recess 3014 of the second electrode case. In the embodiment, the holding member 3110 does not protrude to the surface of the case 3010, and the surface of the case 3010 functions as the gap regulating portion. Note that, a configuration may be possible in which the thickness of the holding member 3110 is made thicker, which causes the holding member 3110 to protrude to the surface of the case 3010, and the dent on the outer side (on the front side) of the recess 3014 functions as a first gap regulating portion, and the holding member 3110 functions as a second gap regulating portion. For example, in arranging the electrodes in the same shape side by side and installing the electrodes on the device, pressing the sealing member at a pressure in a specified range (e.g. 5 to 50 N) causes the gap regulating portion to be contacted with a second electrode case. Thus, the gap regulating portion serves to keep a constant gap between the electrodes and to prevent the sealing member from being excessively pressed.

With this structure, in installing a combination of the electrodes on the device, the sealing member is moderately pressed against the passage connecting recess of the other electrode, and the sealing member is sealed to near the passage. Thus, the residing sample liquid is greatly decreased. Even though the electrodes are installed on a device having a different pressing pressure, the sealing member is uniformly pressed, allowing stable connection of the passages. In the embodiment, an elastic material, polyoxymethylene (POM), was used to form the holding member 3110. The outer diameter of the holding member 3110 was slightly greater than the inner diameter of the dent on the outer side of the recess 3014. Thus, the holding member 3110 functions as a C-ring. The holding member 3110 has the effect that can efficiently hold the sealing member only by fitting the holding member 3110 into the dent on the outer side of the recess 3014 of the electrode case 3010. Alternatively, a configuration may be possible in which for the material of the holding member 3110, rigid polyvinyl chloride, which is the same as the material of the electrode case, is used, the holding member 3110 is formed in a simple doughnut shape, without providing the slit 3111, the holding member 3110 is attached to the dent on the outer side of the recess 3014 of the electrode case 3010 by ultrasonic wave welding, for example, and then the holding member 3110 is integrated with the electrode case. In replacing and handling the electrode, the detachment of the sealing member causes complicated manipulation. Thus, reliably holding the sealing member on the electrode case is a significant advantage to a separate type electrode.

In the case where the sealing member is too thin, the absorption of surface roughness of the body fails, causing a reduction in the sealing properties. Consequently, the thickness of the sealing member was set to 0.01 mm or greater. In the embodiment, using the positioning hole 3012, the positions of the passages of a plurality of electrode cases can be accurately disposed to each other. Specifically, a positioning pin (not illustrated) having its outer diameter the same as or slightly smaller than the inner diameter of the positioning hole 3012 is used, and the positioning pin is passed through the positioning hole 3012 of each of the plurality of electrode case. Thus, the positioning holes 3012 of the electrode cases can be aligned on the same axis. The electrode cases can be aligned in such a manner that the passages are aligned on nearly on the same axis by the projection 3004 and the recess 3014 provided with the holding member. With the combined use of the alignment of the positioning holes 3012, the positions of the passages of the plurality of electrode cases can be more accurately disposed. Thus, effects can be exerted, in which the displacement of the passages at the passage connecting units can be prevented and the problems of a remaining liquid possibly caused by displacement, the occurrence of bubbles, and other problems can be avoided.

Figure 2:
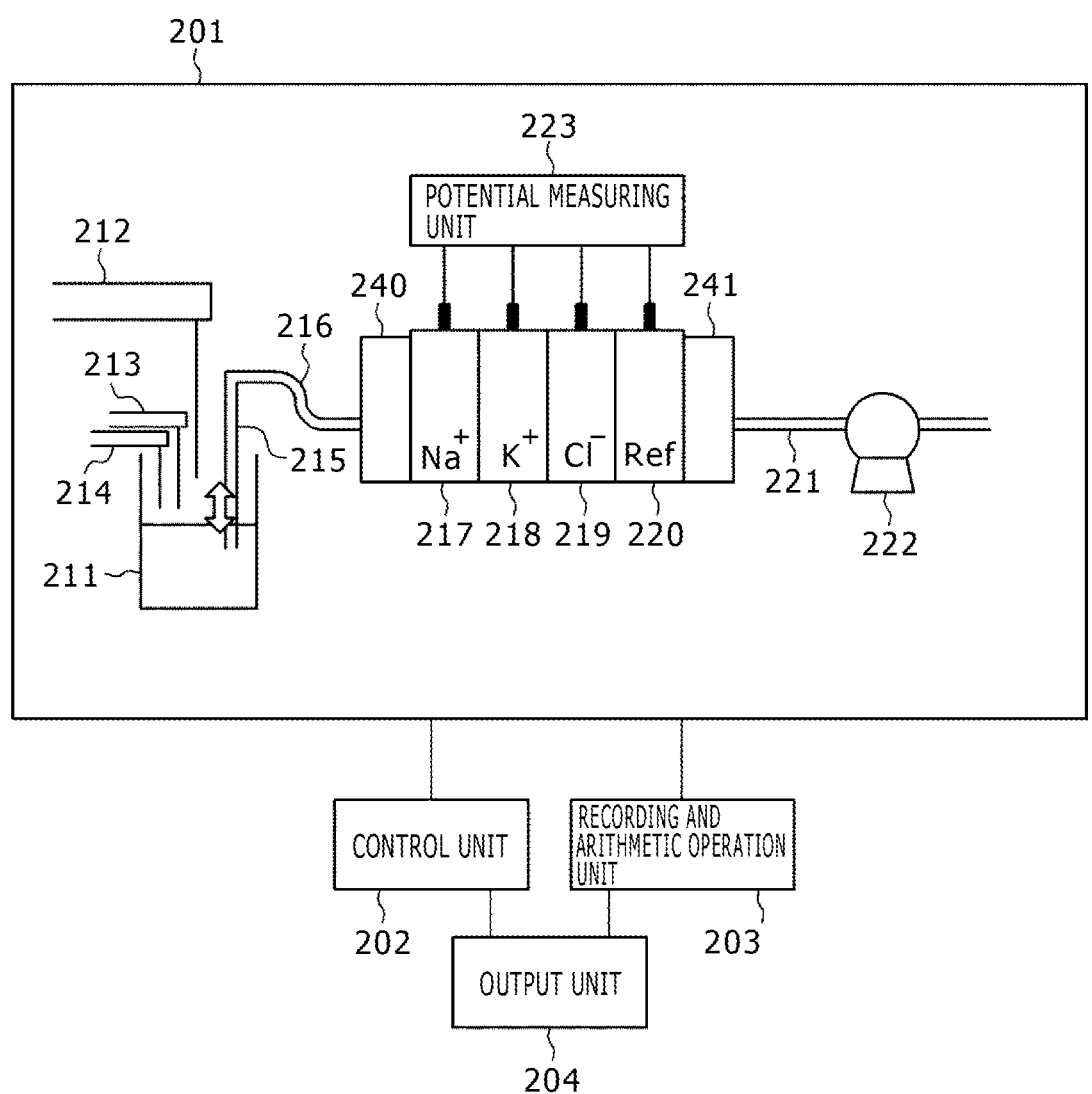
FIG. 2 is a schematic diagram of an example of electrolyte measuring device.

FIG. 2 is a schematic diagram of an example of electrolyte measuring device using the ion selective electrode in FIG. 1.

To a measuring unit 201, a control unit 202, an arithmetic operation recording unit 203, and an output unit 204 are connected. The measuring unit 201 includes a dilution vessel 211, a specimen dispensing nozzle 212, a diluent dispensing nozzle 213, an internal standard solution dispensing nozzle 214, a suction nozzle 215, a pipe 216, a sodium ion ($Na^+$) selective electrode 217, a potassium ion ($K^+$) selective electrode 218, a chlorine ion ($Cl^-$) selective electrode 219, a reference (Ref) electrode 220, an upstream side passage connecting unit 240 and a downstream side passage connecting unit 241 for the ion selective electrodes of the measuring unit, a pipe 221, a pump 222, and a potential measuring unit 223.

The specimen dispensing nozzle 212, the diluent dispensing nozzle 213, and the internal standard solution dispensing nozzle 214 discharge a specimen, such as blood and urine, a diluent, and an internal standard solution to the dilution vessel 211. The suction nozzle 215 is vertically movable, and sucks a solution in the dilution vessel 211 by the driving force of the pump 222. The sucked solution is introduced into the passages of the electrodes 217 to 220 through the pipe 216, and discarded through the pipe 221. The terminals of the electrodes are connected to the potential measuring unit 223.

Here, the passage connecting unit for the ion selective electrodes of the measuring unit will be described. First, for comparison, the passage connecting unit of a previously existing measuring unit according to the electrode structure disclosed in Patent Literature 1 will be described.

FIG. 12 are schematic diagrams of an example of previously existing structure of the passage connecting unit of an electrolyte measuring unit. (a) is a diagram of a face perpendicular to the passage of the upstream side passage connecting unit. (b) is a diagram of a cross section taken along chain line A-A' in (a). (c) is a diagram of a face perpendicular to the passage of the downstream side passage connecting unit. (d) is a diagram of a cross section taken along chain line B-B' in (c). The upstream side passage connecting unit includes a passage 1201 penetrated through a case 1210, an O-ring 1202, an electrode relative positioning projection 1212, and a passage connecting projection 1203. The downstream side passage connecting unit includes a passage 1231 penetrated through a case 1230, an electrode relative positioning groove 1213, and a passage connecting recess 1214. For example, in arranging the above electrodes side by side and installing the electrodes on the measuring unit, the O-ring 1202 of the upstream side passage connecting unit of the measuring unit is pressed against the passage connecting recess of the electrode for functioning as a seal that prevents a sample liquid carried through the passage 1201 from leaking.

However, in this structure, the passage 1201 is apart from the O-ring 1202. As described in FIG. 7(d), a gap 720 is produced between the passage 1201 and the O-ring 1202. A sample liquid resides in the gap, and then the subsequent sample liquid is carried. At this time, the previous sample liquid is gradually carried for a while. Carrying a sample liquid in an amount that allows sufficient replacement hardly affects measurement. However, in the case where the amount of a sample liquid is decreased, the remaining liquid that resides in the gap greatly affects measurement.

Here, the structure of the passage connecting unit of the measuring unit according to the embodiment of the present invention will be described.

Figure 13A:
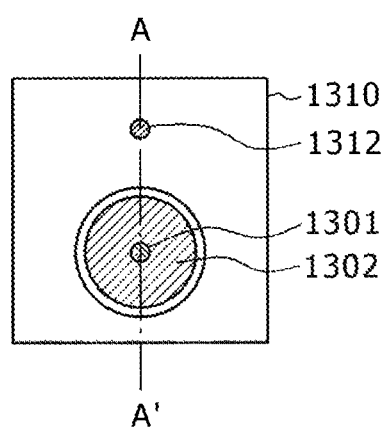
FIGS. 13A and 13B are schematic diagrams of an example of a passage connecting unit of a measuring unit according to the present invention.
Figure 13B:
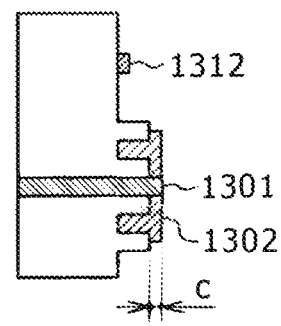

FIG. 13 are schematic diagrams of an example of structure of the passage connecting unit for the ion selective electrode of the measuring unit according to the embodiment of the present invention. (a) is a diagram of a face perpendicular to a passage. (b) is a diagram of a cross section taken along chain line A-A' in (a). The passage connecting unit of the measuring unit is configured of a passage 1301 penetrated through a case 1310, a sealing member 1302, and an electrode relative positioning projection 1312. The sealing member is made of a material softer than the material of the case. The sealing member 1302 has a flat sheet for sealing and a projection for holding and aligning the case 1310. The case has a recess for holding and aligning the sealing member. The sheet is provided with a hole at the position of the passage of the passage connecting unit in the same diameter as the diameter of the cross section of the passage, or greater.

Figure 7A:
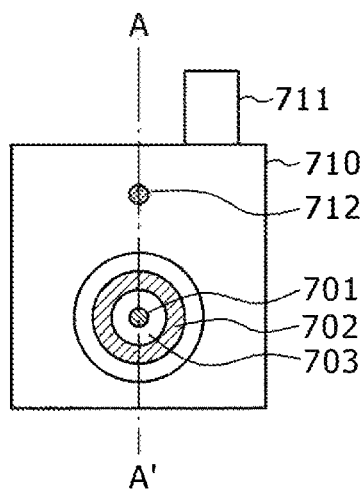
FIGS. 7A-7D are schematic diagrams of an example of a previously existing structure of a passage connecting unit of an ion selective electrode.
Figure 7B:
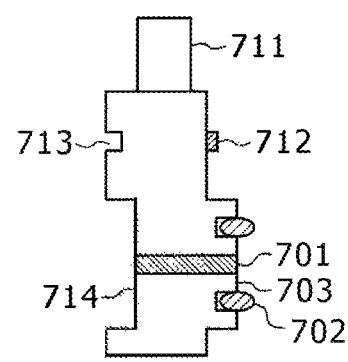
Figure 7C:
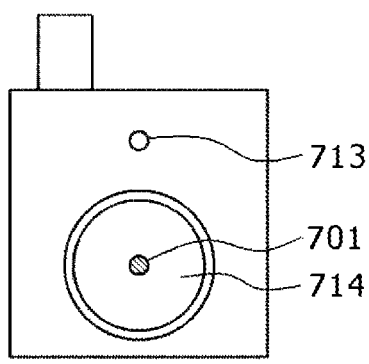
Figure 7D:
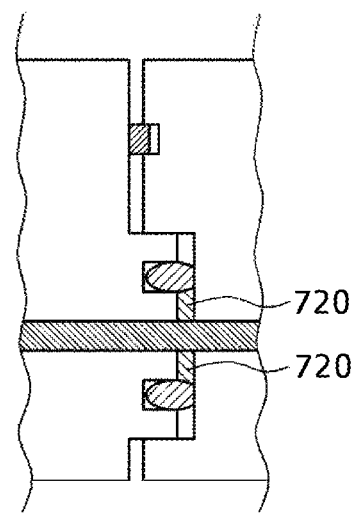

With this structure, for example, in arranging the above electrodes side by side and installing the electrodes on the measuring unit, the sealing member is pressed against the passage connecting recess of the electrode to seal the portion near the passage. Thus, the gap 720 as illustrated in FIG. 7(d) is eliminated, and consequently, the residing sample liquid is greatly decreased. Commonly, a softer sealing member has better adhesion when pressed. However, in order to keep the shape and to maintain the sealing properties even though the pressing pressure is varied, the rubber hardness of the seal is set to 40 or more (durometer type A). The projection of the sealing member is formed in width wider than the width of the alignment recess of the case and in length shorter than the length of the alignment recess. Thus, this allows the efficient integration of the electrodes only by fitting the sealing member 1302 into the case 1310, with no necessity of an adhesive or welding. In replacing the electrode, the detachment of the sealing member of the passage connecting unit of the measuring unit causes complicated manipulation. Thus, reliable holding of the sealing member on the case of the measuring unit is a significant advantage. Only the sealing member can be replaced in the maintenance of the device. The electrode case uses injection molding plastic, and its flat surface accuracy is not so good. Thus, in the case where the sealing member is too thin, the absorption of surface roughness of the body fails, causing a reduction in the sealing properties. Consequently, the thickness c of the sheet was set to 0.01 mm or more.

Figure 14A:
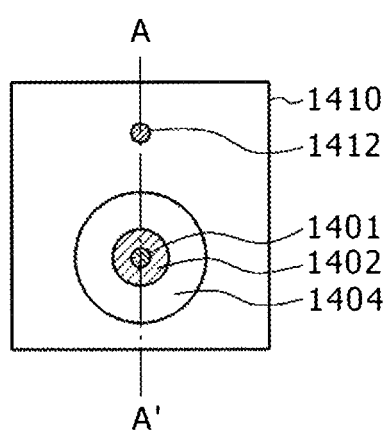
FIGS. 14A and 14B are schematic diagrams of another exemplary structure of a passage connecting unit of a measuring unit according to the present invention.
Figure 14B:
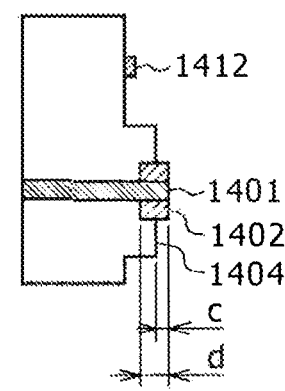

FIG. 14 are schematic diagram of an example of structure of the passage connecting unit of the measuring unit according to the embodiment of the present invention.

(a) is a diagram of a face perpendicular to a passage. (b) is a diagram of a cross section taken along chain line A-A' in (a). The passage connecting unit of the measuring unit is configured of a passage 1401 penetrated through a case 1410, a sealing member 1402, and an electrode relative positioning projection 1412. The sealing member is made of a material softer than the material of the case. The sealing member is provided with a hole at the position of the passage of the passage connecting unit in the same diameter as the diameter of the cross section of the passage, or greater. The case has a recess for holding and aligning the sealing member. The sealing member 1402 is integrated by fitting the sealing member 1402 into the recess for holding the sealing member. The portion near the sealing member on the case provided functions as a gap regulating portion 1404.

For example, in arranging the above electrodes side by side and installing the electrodes on the measuring unit, pressing the sealing member at a pressure in a specified range (e.g. 5 to 50 N) causes the gap regulating portion 1404 to be contacted with the electrode case. Thus, the gap regulating portion 1404 serves to keep the gap to the electrode constant and to prevent the sealing member from being excessively pressed. With this structure, the sealing member is moderately pressed against the passage connecting recess of the electrode, and the sealing member is sealed to near the passage. Thus, the residing sample liquid is greatly decreased. Even though the pressing pressure is varied, the sealing member is uniformly pressed, allowing stable connection of the passages. The outer diameter of the sealing member is formed greater than the inner diameter of the recess of the case for holding the sealing member. Thus, the sealing member 1402 can be efficiently integrated only by fitting the sealing member 1402 into the case 1410. In replacing the electrode, the detachment of the sealing member of the passage connecting unit of the measuring unit causes complicated manipulation. Thus, reliable holding of the sealing member on the case of the measuring unit is a significant advantage. Only the sealing member can be replaced in the maintenance of the device. In the case where the sealing member is too thin, the absorption of surface roughness of the body fails, causing a reduction in the sealing properties. Consequently, the protruding height c of the sealing member was set to 0.01 mm or more. In the case where the collapsing amount of the sealing member is large, the sealing member protrudes and narrows the passage and disturbs the liquid current. Thus, the sealing member was designed in such a manner that a value in which the protruding height c of the sealing member is divided by the total length d of the sealing member is 0.4 or less.

Figure 15A:
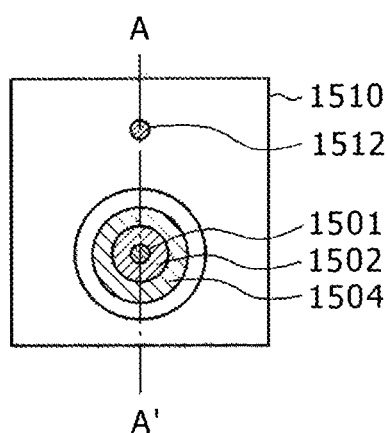
FIGS. 15A and 15B are schematic diagrams of another exemplary structure of a passage connecting unit of a measuring unit according to the present invention.
Figure 15B:
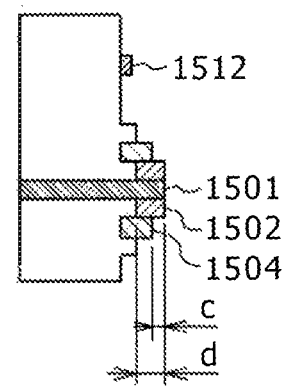

FIG. 15 are schematic diagrams of an example of structure of the passage connecting unit of the measuring unit according to the embodiment of the present invention. (a) is a diagram of a face perpendicular to a passage. (b) is a diagram of a cross section taken along chain line A-A' in (a). The passage connecting unit of the measuring unit is configured of a passage 1501 penetrated through a case 1510, a sealing member 1502, a gap regulating member 1504, and an electrode relative positioning projection 1512. The sealing member is made of a material softer than the material of the case. The gap regulating member is made of a material harder than the material of the sealing member. The sealing member is provided with a hole at the position of the passage of the passage connecting unit in the same diameter as the diameter of the cross section of the passage, or greater. The case has a recess for holding and aligning the gap regulating member. The gap regulating member 1504 is integrated by fitting the gap regulating member 1504 into the recess of the case for holding the gap regulating member. The outer diameter of the sealing member 1502 is formed greater than the inner diameter of the gap regulating member 1504. The sealing member 1502 is integrated by fitting the sealing member 1502 into the gap regulating member 1504. Alternatively in order to more firmly hold the sealing member, the contacting parts of the sealing member to the gap regulating member may be attached in advance by welding or using an adhesive. In replacing the electrode, the detachment of the sealing member of the passage connecting unit of the measuring unit causes complicated manipulation. Thus, reliable holding of the sealing member on the case of the measuring unit is a significant advantage. This structure allows the replacement of only the sealing member in the maintenance of the device.

For example, in arranging the above electrodes side by side and installing the electrodes on the measuring unit, pressing the sealing member at a pressure in a specified range (e.g. 5 to 50 N) causes the gap regulating portion 1504 to be contacted with the electrode case. Thus, the gap regulating portion 1404 serves to keep the gap to the electrode constant and to prevent the sealing member from being excessively pressed. With this structure, the sealing member is moderately pressed against the passage connecting recess of the electrode, and the sealing member is sealed to near the passage. Thus, the residing sample liquid is greatly decreased. Even in a device having a different pressing pressure, the sealing member is uniformly pressed, allowing stable connection of the passages. In the case where the sealing member is too thin, the absorption of surface roughness of the body fails, causing a reduction in the sealing properties. Consequently, the protruding height c of the sealing member is set to 0.01 mm or more. In the case where the collapsing amount of the sealing member is large, the sealing member protrudes and narrows the passage and disturbs the liquid current. Thus, the sealing member was designed in such a manner that a value in which the protruding height c of the sealing member is divided by the total length d of the sealing member is 0.4 or less.

Figure 23A:
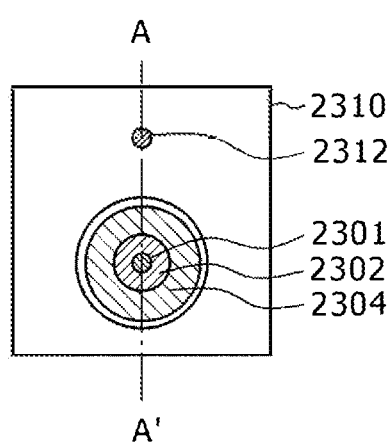
FIGS. 23A and 23B are schematic diagrams of an example of structure of a passage connecting unit of a measuring unit according to the present invention.
Figure 23B:
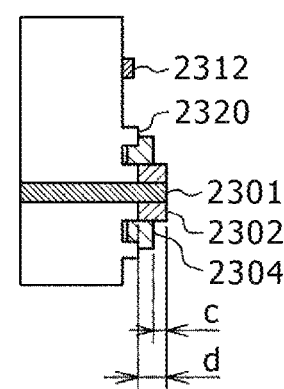

FIG. 23 are schematic diagrams of an example of structure of the passage connecting unit of the measuring unit according to the embodiment of the present invention. The basic configuration is the same as that in FIG. 15. However, the shape of the gap regulating member is different from that in FIG. 15. In FIG. 15, the gap is regulated based on the bottom face of the recess for holding the gap regulating member. In FIG. 23, a gap regulating member 2304 is not in contact with the bottom face of the recess for holding the gap regulating member. The gap regulating member 2304 is in contact with a flat face 2320 of the electrode case for regulating the gap, based on the flat face 2320.

Figure 16A:
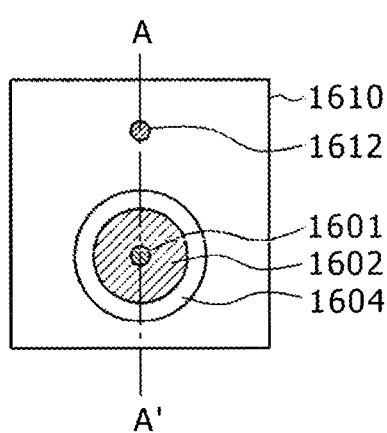
FIGS. 16A and 16B are schematic diagrams of another exemplary structure of a passage connecting unit of a measuring unit according to the present invention.
Figure 16B:
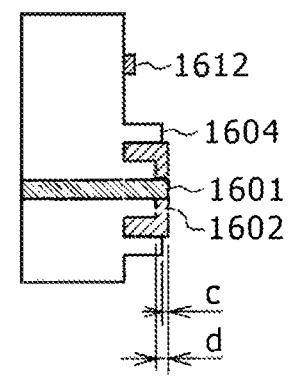

FIG. 16 are schematic diagrams of an example of structure of the passage connecting unit of the measuring unit according to the embodiment of the present invention.

(a) is a diagram of a face perpendicular to a passage. (b) is a diagram of a cross section taken along chain line A-A' in (a). The passage connecting unit of the measuring unit is configured of a passage 1601 penetrated through a case 1610, a sealing member 1602, and an electrode relative positioning projection 1612. The sealing member is made of a material softer than the material of the case. The sealing member 1602 has a flat sheet for sealing and a projection for holding and aligning the case. The case has a recess for holding and aligning the sealing member. The sheet, at the position of the passage of the passage connecting unit, is provided with a hole in the same size as the passage, or greater. The sealing member 1602 is integrated by fitting the sealing member 1602 into the recess of the case 1610 for holding the sealing member. The portion of the case provided with the sealing member functions as a gap regulating portion 1604.

For example, in arranging the above electrodes side by side and installing the electrodes on the measuring unit, pressing the sealing member at a pressure in a specified range (e.g. 5 to 50 N) causes the gap regulating portion 1604 to be contacted with the electrode case. Thus, the gap regulating portion 1404 serves to keep the gap to the electrode constant and to prevent the sealing member from being excessively pressed.

With this structure, the sealing member is moderately pressed against the passage connecting recess of the electrode, and the sealing member is sealed to near the passage. Thus, the residing sample liquid is greatly decreased. Even though the electrodes are installed on a device having a different pressing pressure, the sealing member is uniformly pressed, allowing stable connection of the passages. The projection of the sealing member is formed in width wider than the width of the alignment recess of the case and in length shorter than the length of the alignment recess.

Thus, the sealing member 1602 can be efficiently integrated only by fitting the sealing member 1602 into the case 1610. In replacing the electrode, the detachment of the sealing member of the passage connecting unit of the measuring unit causes complicated manipulation. Thus, reliable holding of the sealing member on the case of the measuring unit is a significant advantage. Only the sealing member can be replaced in the maintenance of the device. In the case where the sealing member is too thin, the absorption of surface roughness of the body fails, causing a reduction in the sealing properties. Consequently, the protruding height c of the sealing member was set to 0.01 mm or more. In the case where the collapsing amount of the sealing member is large, the sealing member protrudes and narrows the passage and disturbs the liquid current. Thus, the sealing member is designed in such a manner that a value in which the protruding height c of the sealing member is divided by the total length d of the sealing member (except the projection) is 0.4 or less.

Here, as examples, the structures of the passage connecting units in FIG. 15 and FIG. 10 are described. However, also in the case where the sealing structure illustrated in FIGS. 24 to 26 is adopted as a joining structure, the similar effect is exerted. Here, the joining structure of the passage connecting unit of the measuring unit to the electrode according to the present invention will be described. First, for comparison, an existing joining structure will be described.

Figure 17A:
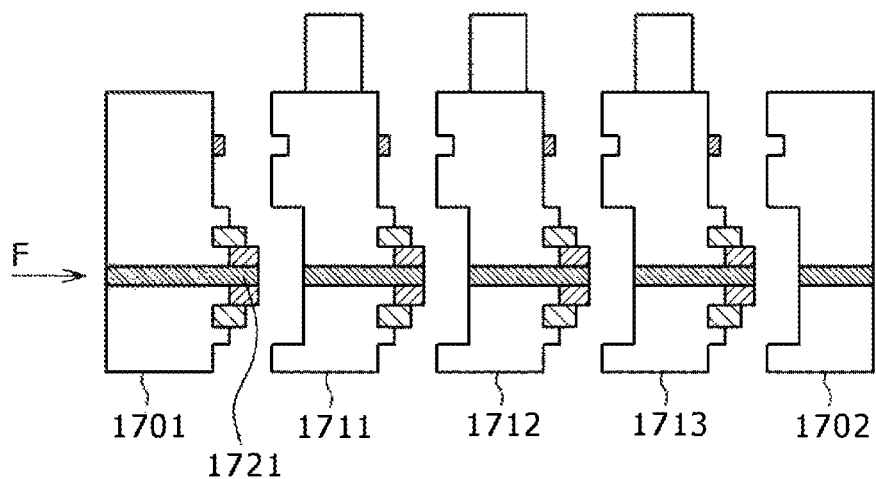
FIGS. 17A and 17B are schematic diagrams of an example of joining structure of a measuring unit to ion selective electrodes.
Figure 17B:
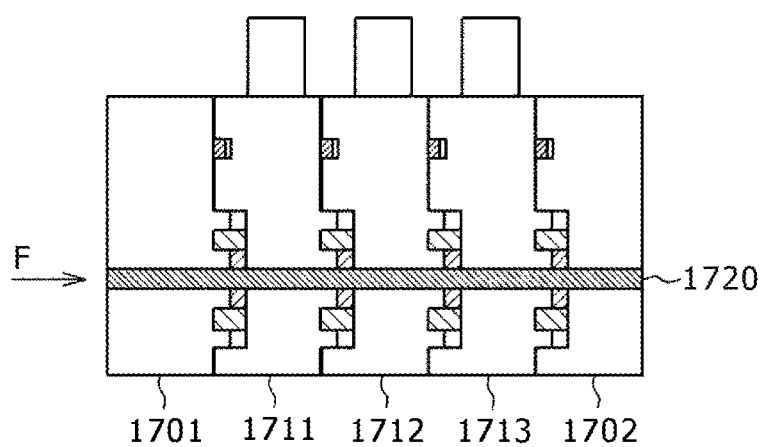

FIG. 17 are schematic diagrams of an example of joining structure of the electrolyte measuring unit to the ion selective electrodes. (a) is a diagram of a state before three electrodes 1711 to 1713 having the structure of the passage connecting unit according to the embodiment of the present invention illustrated in FIG. 10 are arranged between an upstream side passage connecting unit 1701 of the measuring unit according to the embodiment of the present invention illustrated in FIG. 15 and a downstream side passage connecting unit 1702 and pressed from both sides. (b) is a diagram of a state in which the configuration in (a) is pressed from both sides.

In the previously existing joining structure, a liquid is carried from the direction of arrow F to a passage 1720. Thus, in this configuration, the upstream side passage connecting unit 1701 provided with the sealing member is the passage connecting unit on the most upstream side. As described above, the gap at the passage connecting unit on the upstream side greatly affects the measurement accuracy of the surface sensor. Thus, it is desirable to always maintain the sealing member on the upstream side in the excellent state. The ion selective electrode is a consumable item, and replaced periodically. At the same time, the sealing member belonging to the electrode is also replaced.

However, the sealing member 1721 belonging to the passage connecting unit of the measuring unit is not usually replaced. The sealing member 1721 is sometimes replaced in the maintenance of the device, which is the burden to a user or service person. The frequency of replacement of the sealing member 1721 is lower than the frequency of replacement of the electrode.

Figure 18A:
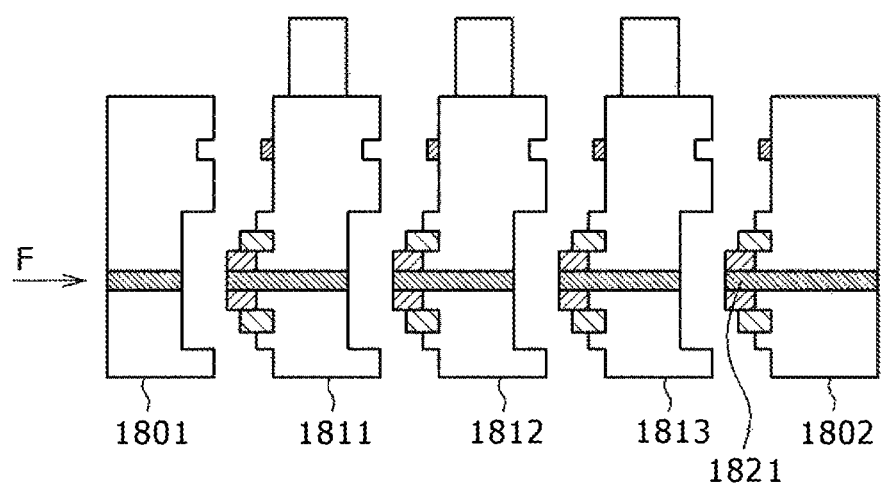
FIGS. 18A and 18B are schematic diagrams of an example of joining structure of a measuring unit to ion selective electrodes according to the present invention.
Figure 18B:
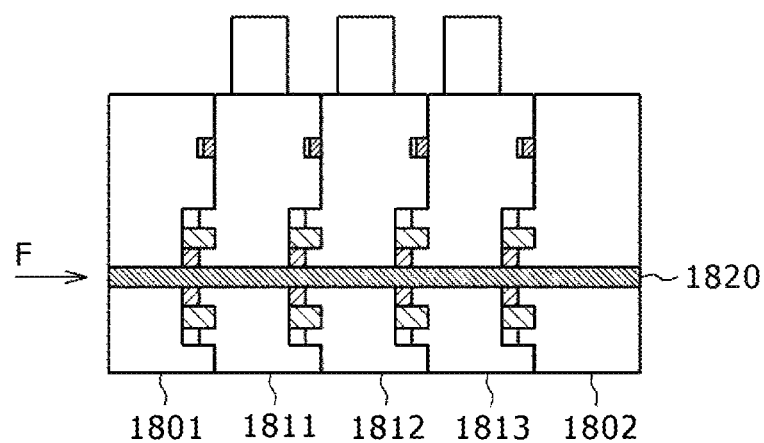

FIG. 18 are schematic diagrams of an example of joining structure of the electrolyte measuring unit to the ion selective electrodes according to the embodiment of the present invention.

(a) is a diagram of a state before three electrodes 1811 to 1813 having the structure of the passage connecting unit illustrated in FIG. 10 are arranged between an upstream side passage connecting unit 1801 and a downstream side passage connecting unit 1802 of the measuring unit illustrated in FIG. 15 and pressed from both sides. (b) is a diagram of a state after the configuration in (a) is pressed from both sides. A liquid is carried from the direction of arrow F to a passage 1820. Thus, in this configuration, the upstream side passage connecting unit 1801 provided with no sealing member is the passage connecting unit on the most upstream side. Therefore, in the structure according to the embodiment of the present invention, at the same time when the ion selective electrode is replaced, the sealing member on the upstream side is also replaced.

On the other hand, in this structure, a sealing member 1821 provided on the upstream side passage connecting unit 1801 of the measuring unit is not periodically replaced. However, even in the state in which the sealing member is degraded, a gap is produced between passages on the most downstream side, and a liquid is prone to reside, the measurement values of the electrodes on the upstream side are hardly affected. Thus, the structure according to the embodiment of the present invention is highly reliable on measurement against the degradation of the sealing member, compared with the previously existing structure. The burden of the user or service person is reduced, and the ease of maintenance is improved. Here, for examples, the joining structures in the structures of the passage connecting units in FIG. 15 and FIG. 10 are described. However, the joining structure according to the embodiment of the present invention also exerts the effect even in other sealing structures.

FIG. 21 are schematic diagrams of an example of joining state of the measuring unit to the ion selective electrodes. (a) is a diagram of a joining state in which in the combination of the ion selective electrode with the upstream side passage connecting unit of the measuring unit in the configuration in FIG. 18, the center axis of a pressing pressure is displaced and the electrodes are tilted and joined to each other. (b) is a diagram of a face perpendicular to the passage of the electrode. The contact area of the passage joining portions of the sealing members is small, and is nearly in point contact, which easily causes the electrodes to be tilted and joined as illustrated in (a). The electrodes are tilted and joined to each other in this manner, which degrades the sealing properties of the passages between the electrodes, resulting in the possibility that a liquid remains or a liquid leaks. In order to maintain the sealing properties with likelihood to the center position or the direction of the pressing pressure of the measuring unit, a tangent angle formed of the passage length of the joined electrodes and the width from the center of the passage to the outer side of the flat face of the sealing part is desirably an angle of two degrees or more (Atan (a/b)≥2°, where a is dimension a illustrated in FIG. 21, b is dimension b illustrated in FIG. 21, and Atan is an inverse trigonometric function).

In the structure according to the embodiment of the present invention, the frequency, in which the sealing member is contacted with a liquid carried through the passage, is more increased than in the previously existing structure. Thus, taking into account of resistance to hypochlorous acid, which is one of detergents, the material of the sealing member was selected from rubbers having a polymethylene type main chain or rubbers having silicon and oxygen on their main chain for use, which correspond to M group and Q group in JIS. Specifically, a rubber having a polymethylene type main chain includes, for example, a rubber copolymer (acrylic rubber) containing a small amount of a monomer vulcanizable with acrylic acid ethyl or other acrylic acid esters, a rubber copolymer containing acrylic acid ethyl or other acrylic acid esters and ethylene, a rubber copolymer containing acrylic acid ethyl or other acrylic acid esters and acrylonitrile, a rubber copolymer containing chlorinated polyethylene, chlorosulfonated polyethylene, ethylene, propylene, and diene, a rubber copolymer containing ethylene and propylene, a rubber copolymer containing ethylene and vinyl acetate, a rubber copolymer containing ethylene tetrafluoride and propylene, a rubber copolymer containing being fluoro and a perfluoro alkyl group or a perfluoro alkoxy group on all of its side chains, a rubber copolymer containing fluoro and a perfluoro alkyl group or a perfluoro alkoxy group on its side chain, a rubber copolymer containing polyisobutene or polyisobutylene, acrylonitrile having a fully hydrogenated main chain, and butadiene, a rubber copolymer containing styrene, ethylene, and butene, and a rubber copolymer containing styrene, ethylene, and propylene. A rubber having silicon and oxygen on its main chain includes, for example, a silicone rubber containing a methyl substituent group and a fluoro substituent group on its polymer chain, a silicone rubber (fluorosilicone rubber) containing a methyl substituent group, vinyl, and a fluoro substituent group on its polymer chain, a silicone rubber (polydimethylsiloxane) containing a methyl substituent group on its polymer chain, a silicone rubber containing a methyl substituent group and a phenyl substituent group on its polymer chain, a silicone rubber containing a methyl substituent group, a vinyl substituent group, and a phenyl substituent group on its polymer chain, and a silicone rubber containing a methyl substituent group and a vinyl substituent group on its polymer chain.

Figure 4:
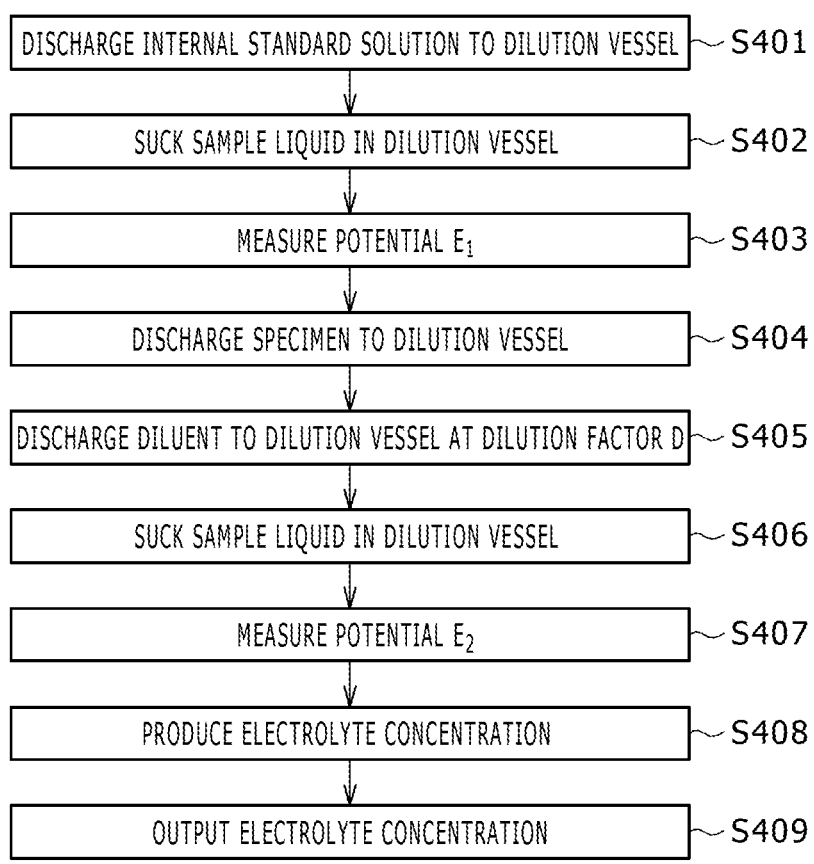
FIG. 4 is a diagram of an example of flowchart of the process steps of electrolyte concentration measurement.

FIG. 4 is a diagram of an example of flowchart of process steps performed by the control unit 202 in electrolyte concentration measurement using the electrolyte measuring device in FIG. 2.

An internal standard solution is discharged to the dilution vessel 211 using the internal standard solution dispensing nozzle 214 (S401). The internal standard solution in the dilution vessel 211 is sucked using the suction nozzle 215 and the pump 222 (S402). Thus, the passages of the electrodes 217 to 220 are filled with the internal standard solution. The potentials of the electrodes 217 to 219 are measured based on the reference electrode 220 using the potential measuring unit 223, and the potentials are set to $E_{1,n}$ (n is ions) (S403). A specimen is discharged to the dilution vessel 211 using the specimen dispensing nozzle 212 (S404). A diluent is discharged to the dilution vessel 211 using the diluent dispensing nozzle 213 (S405).

Thus, the specimen is diluted in a ratio D of the specimen amount to the diluent amount. A sample liquid in the dilution vessel is sucked using the suction nozzle 215 and the pump 222 (S406). The passages of the electrodes 217 to 220 are filled with the sample liquid. The potentials of the electrodes 217 to 219 are measured based on the reference electrode 220 using the potential measuring unit 223, and the potentials are set to $E_{2,n}$ (S407). From the potentials $E_{1,n}$ and $E_{2,n}$, the ratio D, and a measurement target ion concentration $c_{IS,n}$ in the internal standard solution, a measurement target ion concentration $c_n$ in the specimen is calculated using Equation below based on the Nernst equation (S408), where z is defined as the valence of the measurement target ion, F is defined as a Faraday constant, R is defined as a gas constant, and T is defined as a absolute temperature.

$$c_n = Dc_{IS,n} \exp(zF/RT(E_{2,n}-E_{1,n}))$$

The calculated concentration is outputted by a method, such as outputting the value on a screen and by printing (S409).

For the diluent, a diluent containing no measurement target ion, for example, is used, including a tris-borate buffer and a bis-tris-borate buffer (e.g. Japanese Unexamined Patent Application Publication No. Hei 5-209857). For the internal standard solution, an internal standard solution can be used, for example, in which a measurement target ion at about a blood concentration reference value, which is a solution of sodium 140 mM, a solution of potassium 4 mM, or a solution of chlorine 100 mM, is thought as a specimen, and the solution is diluted with a diluent at a dilution factor D.

Figure 5:
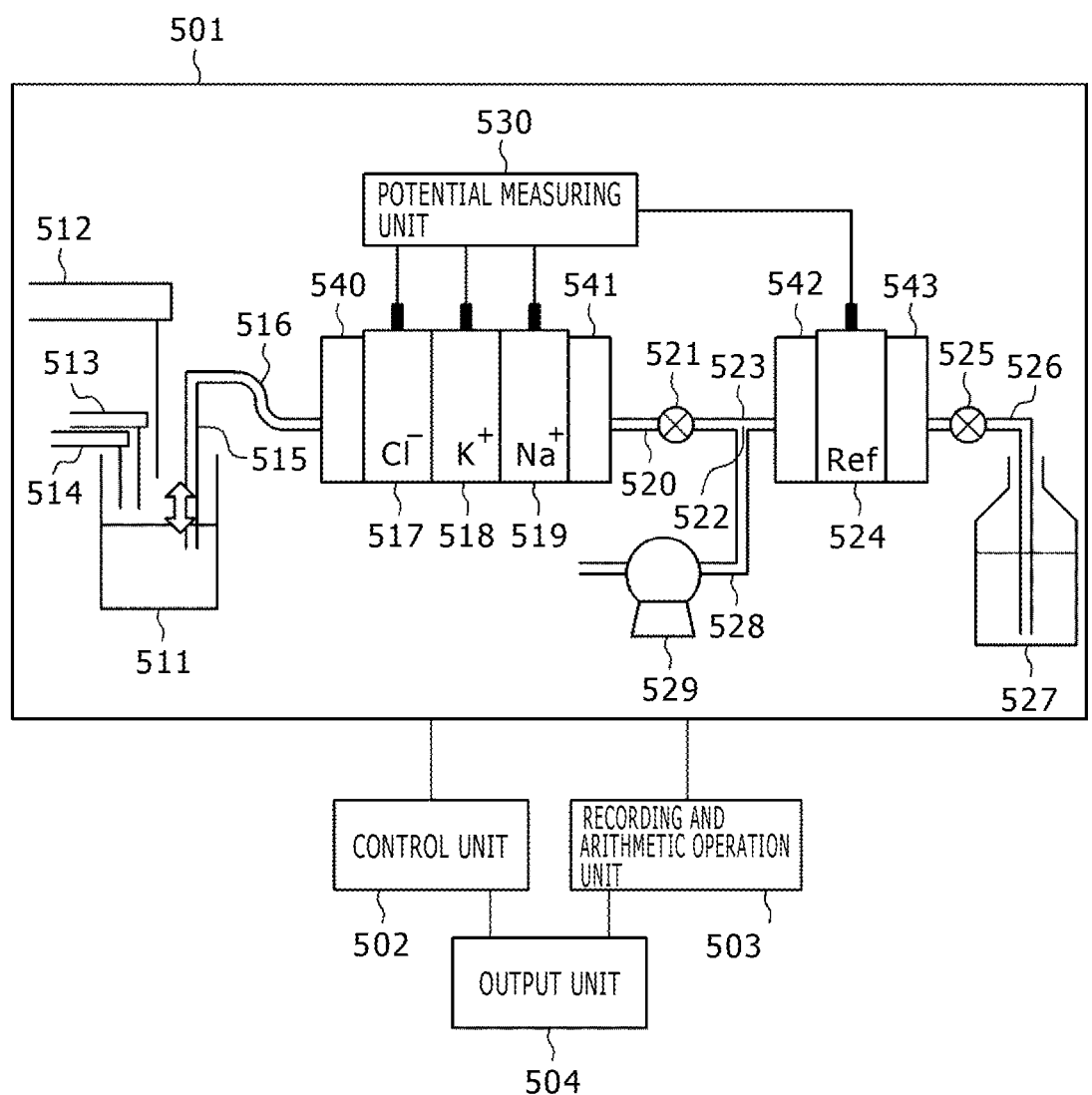
FIG. 5 is a schematic diagram of another exemplary electrolyte measuring device.

FIG. 5 is a schematic diagram of an example of electrolyte measuring device using the ion selective electrodes having the passage connecting units in FIGS. 8 to 11. To a measuring unit 501, a control unit 502, an arithmetic operation recording unit 503, and an output unit 504 are connected. The measuring unit 501 includes a dilution vessel 511, a specimen dispensing nozzle 512, a diluent dispensing nozzle 513, an internal standard solution dispensing nozzle 514, a suction nozzle 515, a pipe 516, a chlorine ion selective electrode 517, a potassium ion selective electrode 518, a sodium ion selective electrode 519, an upstream side passage connecting unit 540 and a downstream side passage connecting unit 541 for ion selective electrodes of the measuring unit in the structure of the passage connecting unit in FIGS. 13 to 16, a pipe 520, a valve 521, a junction 522, a pipe 523, a reference electrode 524, an upstream side passage connecting unit 543 and a downstream side passage connecting unit 542 for a reference electrode having the structure of the passage connecting unit in FIGS. 13 to 16, a valve 525, a pipe 526, a reference liquid 527, a pipe 528, a pump 529, and a potential measuring unit 530. The joining structure of the electrolyte measuring unit to the ion selective electrodes in FIG. 18 is used.

The specimen dispensing nozzle 512, the diluent dispensing nozzle 513, and the internal standard solution dispensing nozzle 514 discharge a specimen such as blood and urine, a diluent, and an internal standard solution to the dilution vessel 511. The suction nozzle 515 is vertically movable, and sucks a solution in the dilution vessel 511 using the driving force of the pump 529. In the case where the valve 521 is opened and the valve 525 is closed, the sucked solution is introduced into the passages of the electrodes 517 to 519 through the pipe 516, and is discarded through the pipe 520, the junction 522, and the pipe 528.

In the case where the pump 529 is driven when the valve 521 is closed and the valve 525 is opened, the reference liquid 527 is sucked through the pipe 526, introduced into the passage of the reference electrode 524, and then discarded through the pipe 523, the junction 522, and the pipe 528. The terminals of the electrodes 517 to 519 and 524 are connected to the potential measuring unit 530. For the potential measuring unit 530, one similar to FIG. 3 can be used. For the reference electrode 524, in addition to the reference electrode using porous glass or ceramics described in FIG. 2, a configuration may be possible in which the ion selective electrode is used for the reference electrode 524, and the electrolyte concentration in the reference liquid 527 corresponding to the reference electrode 524 is made constant. Note that, only one kind of reference liquid is carried through the passage of the reference electrode. Thus, a liquid residing in the gap between the passages hardly affects the measured result. Therefore, applying the structure according to the embodiment of the present invention to the reference electrode, the upstream side passage connecting unit 542, and the downstream side passage connecting unit 543 for the reference electrode exerts poor effect. The structure according to the embodiment of the present invention is applied to the passage connecting unit through which two kinds or more liquids, and thus a better effect of the embodiment of the present invention is exerted.

Figure 6:
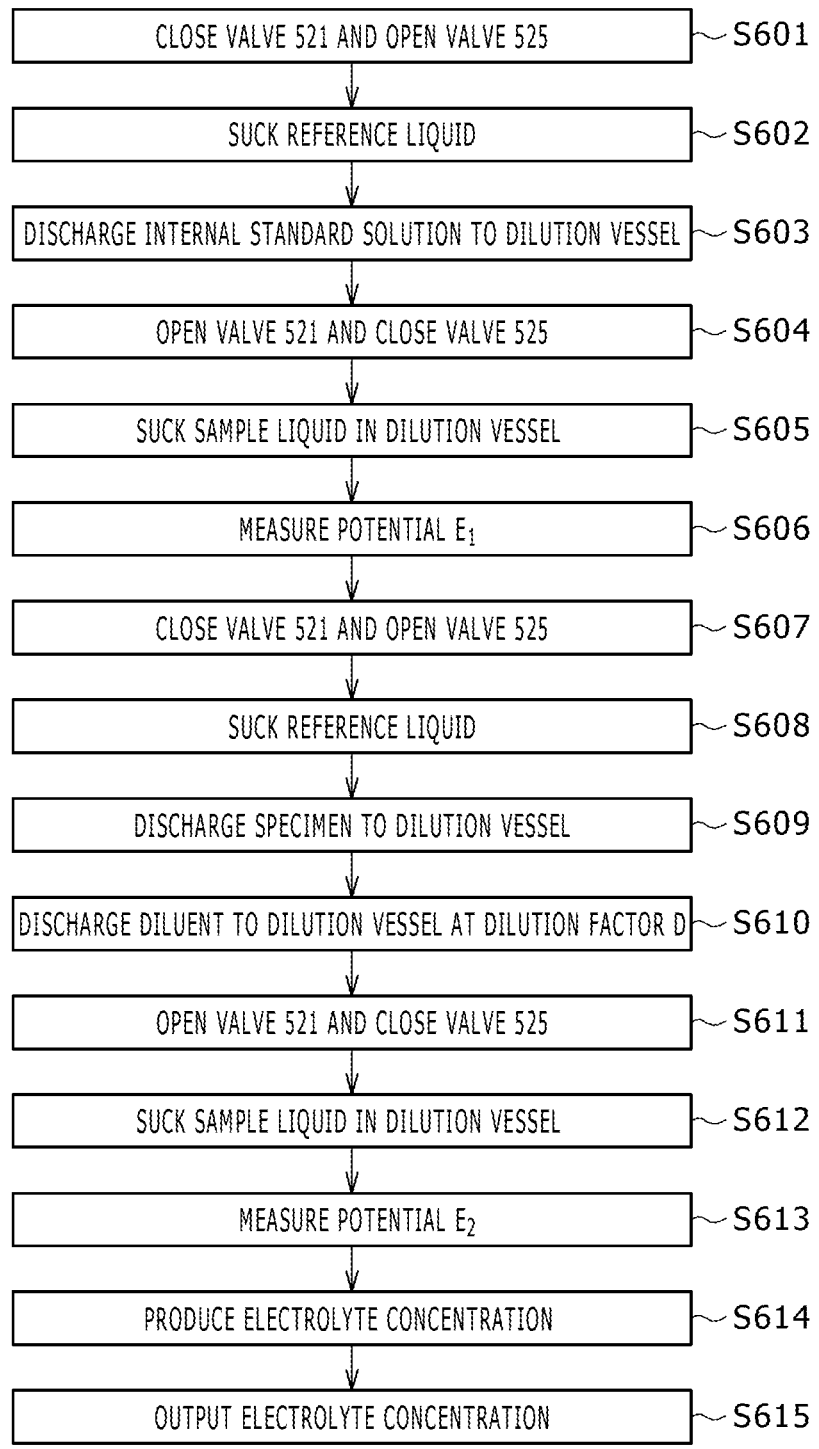
FIG. 6 is a diagram of an example of flowchart of the process steps of electrolyte concentration measurement.

FIG. 6 is a diagram of an example of flowchart of process steps performed by the control unit 502 in electrolyte concentration measurement using the electrolyte measuring device in FIG. 5.

The valve 521 is closed, and the valve 525 is opened (S601). The reference liquid 527 is sucked using the pump 529 (S602). Thus, the passage of the reference electrode 524, the pipe 523, and the junction 522 are filled with the reference liquid. The internal standard solution is discharged to the dilution vessel 511 using the internal standard solution dispensing nozzle 514 (S603). The valve 521 is opened, and the valve 525 is closed (S604). The internal standard solution in the dilution vessel 511 is sucked using the suction nozzle 515 and the pump 529 (S605).

Thus, the passages of the electrodes 517 to 519, the pipe 520, and the junction 522 are filled with the internal standard solution. At this time, the electrodes 517 to 519 and the reference electrode 524 are connected to the pipes 520 and 523 and the junction 522 filled with the solution. Thus, the potential $E_{1,n}$ of each of the electrodes 517 to 519 can be measured based on the reference electrode 524 using the potential measuring unit 530 (S606).

Similarly, the valve 521 is closed, and the valve 525 is opened (S607). The reference liquid 527 is sucked using the pump 529 (S608), and then the specimen is discharged to the dilution vessel 511 using the specimen dispensing nozzle 512 (S609). The diluent is discharged to the dilution vessel 511 using the diluent dispensing nozzle 513 (S610). Thus, the specimen is diluted in the ratio D of the specimen amount to the diluent amount. The valve 521 is opened, and the valve 525 is closed (S611). The sample liquid in the dilution vessel 511 is sucked using the suction nozzle 515 and the pump 529 (S612).

Thus, the passages of the electrodes 517 to 519, the pipe 520, and the junction 522 are filled with the sample liquid. The potential $E_{2,n}$ of each of the electrodes 517 to 519 is measured based on the reference electrode 524 using the potential measuring unit 530 (S613). From the potentials of $E_{1,n}$ and $E_{2,n}$, the ratio D, and the measurement target ion concentration $c_{IS,n}$ in the internal standard solution, a measurement target ion concentration $c_n$ in the specimen is calculated using Equation below based on the Nernst equation (S614), where z is defined as the valence of the measurement target ion, F is defined as a Faraday constant, R is defined as a gas constant, and T is defined as a absolute temperature.

$$c_n = Dc_{IS,n}\exp(zF/RT(E_{2,n}-E_{1,n}))$$

The calculated concentration is outputted by a method such as outputting the value on a screen and by printing (S615).

FIG. 20 is a diagram of a result of remaining liquid confirmation experiments. A measurement method is in which a high concentration sample H was measured, a low concentration sample L, whose concentration was one-hundredth of the high concentration sample, and then a remaining liquid r was calculated from the measured concentrations using an equation below.

$$c_{meas} = rc_H + c_L$$

Here, $c_{meas}$ is defined as the measured value of the low concentration sample, $c_H$ is defined as the concentration of the high concentration sample, $c_L$ is defined as the concentration of the low concentration sample, and r is defined as the remaining liquid.

FIG. 20 is a diagram of a result of remaining liquid amount confirmation experiments. Remaining liquid amounts were compared among a liquid replacement amount of 350 μL in the previously existing structure and a liquid replacement amount of 350 μL and a liquid replacement amount of 175 μL, which was a half of 350 μL, in the structure according to the embodiment of the present invention. As a result, in the previously existing structure, a remaining liquid was observed in the average of 0.69% and in the standard deviation of 0.02%. In the structure according to the embodiment of the present invention, in the liquid replacement amount of 350 μL, a remaining liquid was observed in the average of 0.28% and the standard deviation of 0.07%. In the liquid replacement amount of 175 μL, a remaining liquid was observed in the average of 0.30% and the standard deviation of 0.14%. In other words, the structure according to the embodiment of the present invention demonstrated that even in a half of the liquid replacement amount, measurement accuracy equivalent to or more than that in the previously existing structure could be maintained.

Figure 3A:
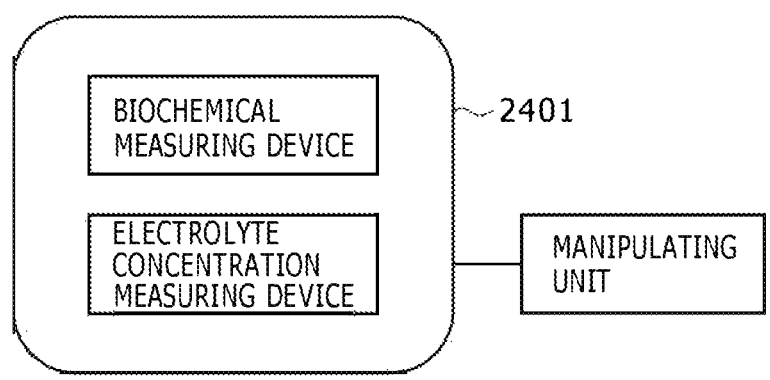
FIGS. 3A and 3B are diagrams of an example of an electrolyte measurement system using an electrolyte concentration measuring device.
Figure 3B:
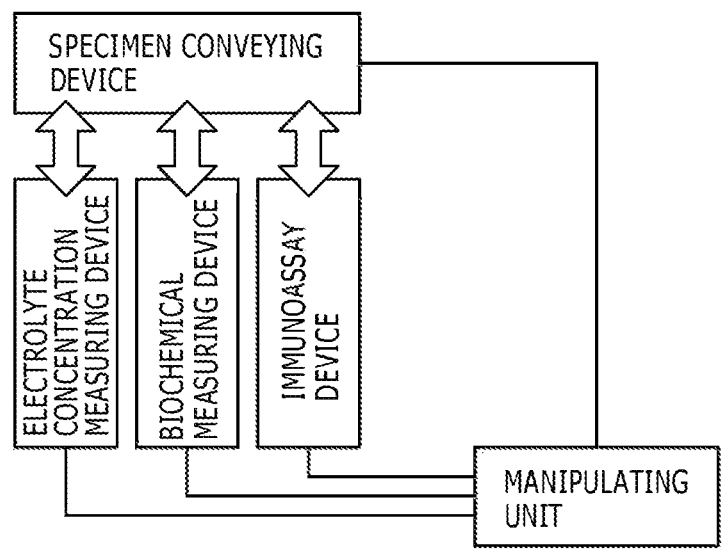

FIG. 3 are diagrams of examples of electrolyte measurement systems using the electrolyte concentration measuring device.

(a) is a diagram of a biochemical automatic analyzer 2401 installed with a biochemical measuring device used mainly for optical measurement and the electrolyte concentration measuring device according to the embodiment of the present invention. The biochemical automatic analyzer 2401 can be controlled from a manipulating unit. (b) is a diagram of the electrolyte concentration measuring device, a biochemical measuring device, an immunoassay device, and other devices, which are independent devices, in which a specimen is carried between these devices and a specimen conveying device. The devices can be controlled from a manipulating unit.

Note that, the present invention is not limited to the foregoing embodiments. The present invention includes various exemplary modifications. For example, in the foregoing embodiments, the present invention is described in detail for easy understanding. The present invention is not necessarily limited to ones including all the described configurations. A part of the configuration of an embodiment can be replaced by the configuration of another embodiment. The configuration of an embodiment can be added with the configuration of another embodiment. A part of the configurations of the embodiments can be added with, deleted from, or replaced by the other configurations.

LIST OF REFERENCE SIGNS

101: case of ion selective electrode,
102: passage,
103: silver-silver chloride electrode,
104: internal liquid,
105: sensitive membrane,
201, 501: measuring unit,
202, 502: control unit,
203, 503: arithmetic operation recording unit,
204, 504: output unit,
211, 511: dilution vessel,
212, 512: specimen dispensing nozzle,
213, 513: diluent dispensing nozzle,
214, 514: internal standard solution dispensing nozzle,
215, 515: suction nozzle,
216, 221, 516, 520, 523, 526, 528: pipe,
217, 519: sodium ion selective electrode,
218, 518: potassium ion selective electrode,
219, 517: chlorine ion selective electrode,
220, 524: reference electrode,
222, 529: pump,
223, 530: potential measuring unit,
521, 525: valve,
522: junction,
527: reference liquid,
240, 540, 543, 1701, 1801: upstream side passage connecting unit, 241, 541, 542, 1702, 1802: downstream side passage connecting unit,
702, 1202: O-ring,
703, 1203: passage connecting projection,
701, 801, 901, 1001, 1101, 3001: passage,
802, 902, 1002, 1102, 3100: sealing member,
710, 810, 910, 1010, 1110, 3010: electrode case,
711, 811, 911, 1011, 1111, 3011: terminal,
712, 812, 912, 1012, 1112: electrode relative positioning projection,
713, 813, 913, 1013, 1113, 1213: electrode relative positioning groove,
714, 814, 914, 1014, 1114, 1214, 3014: passage connecting recess,
904, 1104, 1404, 1604: gap regulating portion,
1004, 1504: gap regulating member,
1201, 1231, 1301, 1401, 1501, 1601: passage,
1302, 1402, 1502, 1602: sealing member,
1210, 1230, 1310, 1410, 1510, 1610: case,
1212, 1312, 1412, 1512, 1612: electrode relative positioning projection,
1711, 1712, 1713, 1811, 1812, 1813: electrode,
2401: biochemical automatic analyzer,
3004: passage connecting projection,
3005: sensitive membrane attaching portion,
3012: positioning hole,
3024: space,
3110: holding member,
3111: slit.

The invention claimed is:

1. A device for measuring a sample liquid using an ion selective electrode, the device comprising:
an upstream side passage connection unit; and
a sealing member,
wherein the upstream side passage connection unit comprises:
a first passage penetrated through the upstream side passage connection unit; and
a passage connecting unit, configured to connect a second passage provided on the ion selective electrode,
wherein the passage connecting unit includes the sealing member for sealing a gap between the first passage of the upstream side passage connection unit and the second passage of the ion selective electrode,
wherein the sealing member is integrally formed of:
a sheet portion having a first surface connecting the upstream side passage connection unit and a second surface configured to connect the ion selective electrode, the sheet portion having an opening; and
a projection portion that projects from the sheet portion;
wherein rubber hardness of the sealing member is lower than rubber hardness of the upstream side passage connection unit, and
wherein the upstream side passage connection unit has a recess holding the projection portion of the sealing member so that the opening of the sheet portion is attached to an end portion of the first passage of the upstream side passage connection unit.

2. The device according to claim 1, wherein one side surface of the recess has an open end in contact with the first passage of the upstream side passage connection unit.

3. The device according to claim 1, wherein one side surface of the recess does not have an open end in contact with the first passage of the upstream side passage connection unit.

4. The device according to claim 1, further comprising:
an electrode relative positioning projection disposed on a same side of the upstream side passage connection unit as the sealing member.

5. The device according to claim 1, wherein the material of the sealing member is a rubber having a polymethylene type main chain, a rubber having silicon and oxygen on a main chain.

6. The device according to claim 1, wherein the material of the sealing member is a rubber copolymer containing polyethylene, ethylene, propylene, and diene.

7. The device according to claim 1, wherein the material of the sealing member is:
a rubber copolymer containing fluoro and a perfluoro alkyl group, or a perfluoro alkoxy group, on all of its side chains, or
a rubber copolymer containing fluoro and a perfluoro alkyl group, or a perfluoro alkoxy group, on its side chain.

8. An device for measuring a sample liquid using an ion selective electrode, the device comprising:
a downstream side passage connection unit; and
a sealing member,
wherein the downstream side passage connection unit comprises:
a first passage penetrated through the downstream side passage connection unit; and
a passage connecting unit, configured to connect a second passage provided on the ion selective electrode,
wherein the passage connecting unit includes the sealing member for sealing a gap between the first passage of the downstream side passage connection unit and the second passage of the ion selective electrode,
wherein the sealing member is integrally formed of:
a sheet portion having a first surface connecting the downstream side passage connection unit and a second surface configured to connect the ion selective electrode, the sheet portion having an opening; and
a projection portion that projects from the sheet portion;
wherein rubber hardness of the sealing member is lower than rubber hardness of the downstream side passage connection unit, and
wherein the downstream side passage connection unit has a recess holding the projection portion of the sealing member so that the opening of the sheet portion is attached to an end portion of the first passage of the downstream side passage connection unit.

9. The device according to claim 8, wherein one side surface of the recess has an open end in contact with the first passage of the downstream side passage connection unit.

10. The device according to claim 8, wherein one side surface of the recess does not have an open end in contact with the first passage of the downstream side passage connection unit.

11. The device according to claim 8, further comprising:
an electrode relative positioning projection disposed on a same side of the downstream side passage connection unit as the sealing member.

12. The device according to claim 8, wherein the material of the sealing member is a rubber having a polymethylene type main chain, a rubber having silicon and oxygen on a main chain.

13. The device according to claim 8, wherein the material of the sealing member is a rubber copolymer containing polyethylene, ethylene, propylene, and diene.

14. The device according to claim 8, wherein the material of the sealing member is:
- a rubber copolymer containing fluoro and a perfluoro alkyl group, or a perfluoro alkoxy group, on all of its side chains, or
- a rubber copolymer containing fluoro and a perfluoro alkyl group, or a perfluoro alkoxy group, on its side chain.

* * * * *